(12) United States Patent
DeGheest et al.

(10) Patent No.: US 8,407,065 B2
(45) Date of Patent: Mar. 26, 2013

(54) WOUND CARE TREATMENT SERVICE USING AUTOMATIC WOUND DRESSING FABRICATOR

(75) Inventors: Anne DeGheest, Los Altos Hills, CA (US); Dmitriy Sinyagin, New York, NY (US)

(73) Assignee: PolyRemedy, Inc., San Jose, CA (US)

( * ) Notice: Subject to any disclaimer, the term of this patent is extended or adjusted under 35 U.S.C. 154(b) by 399 days.

(21) Appl. No.: 12/110,228

(22) Filed: Apr. 25, 2008

(65) Prior Publication Data

US 2009/0204423 A1    Aug. 13, 2009

Related U.S. Application Data

(63) Continuation-in-part of application No. 10/431,888, filed on May 7, 2003.

(60) Provisional application No. 60/378,635, filed on May 7, 2002.

(51) Int. Cl.
   *G06Q 50/00* (2006.01)
(52) U.S. Cl. .......................................................... 705/2
(58) Field of Classification Search .................. 705/2–4
   See application file for complete search history.

(56) References Cited

U.S. PATENT DOCUMENTS

| | | |
|---|---|---|
| 2,682,873 A | 7/1954 | Idnis |
| 2,836,178 A | 5/1958 | Barr |
| 3,140,572 A | 7/1964 | Petersen et al. |
| 3,425,412 A | 2/1969 | Pope |
| 3,729,892 A | 5/1973 | Aslund et al. |
| 3,811,445 A | 5/1974 | Dostal |
| 4,347,841 A | 9/1982 | Benyo et al. |
| 4,522,203 A | 6/1985 | Mays |
| 4,630,426 A | 12/1986 | Gentry |
| 4,751,133 A | 6/1988 | Szycher et al. |
| 4,869,936 A | 9/1989 | Moskowitz et al. |
| 4,906,240 A | 3/1990 | Reed et al. |
| 4,917,688 A | 4/1990 | Nelson et al. |
| 4,948,540 A | 8/1990 | Nigam |
| 4,957,795 A | 9/1990 | Riedel |
| 5,000,172 A | 3/1991 | Ward |
| 5,265,605 A | 11/1993 | Afflerbach |
| 5,340,363 A | 8/1994 | Fabo |
| 5,395,305 A | 3/1995 | Koide et al. |
| 5,480,377 A | 1/1996 | Cartmell et al. |
| 5,489,437 A | 2/1996 | Marra |
| 5,520,735 A | 5/1996 | Mulder |
| 5,520,762 A | 5/1996 | Rasmussen et al. |
| 5,588,428 A | 12/1996 | Smith et al. |

(Continued)

FOREIGN PATENT DOCUMENTS

| | | |
|---|---|---|
| GB | 1221282 A | 2/1971 |
| WO | WO 00/43046 A2 | 7/2000 |

OTHER PUBLICATIONS

"Iterations" from www.wikipedia.com.*

(Continued)

*Primary Examiner* — John Pauls
(74) *Attorney, Agent, or Firm* — Fenwick & West LLP

(57) ABSTRACT

A method and/or system allowing patients to receive consistent, effective and convenient reliable wound care by applying customized wound dressings fabricated at automatic wound dressing fabricators deployed in medical facilities. Wound dressing specifications are generated with the aid of a computer-based configuration algorithm based on characteristics of the wounds. The generated wound dressing specifications are communicated between the medical facilities to provide consistent and reliable wound dressings without duplicative diagnosis of the wound. Further, telemedicine for wound care may be implemented by communicating the wound dressing specifications to automatic wound dressing fabricators that are remotely located.

44 Claims, 13 Drawing Sheets

U.S. PATENT DOCUMENTS

| | | | |
|---|---|---|---|
| 5,641,501 | A | 6/1997 | Cooper et al. |
| 5,653,699 | A | 8/1997 | Reed et al. |
| 5,681,579 | A | 10/1997 | Freeman |
| 5,741,509 | A | 4/1998 | Kushner |
| 5,757,498 | A | 5/1998 | Klein, II et al. |
| 5,762,620 | A | 6/1998 | Cartmell et al. |
| 5,785,697 | A | 7/1998 | Trombetta et al. |
| 5,891,078 | A | 4/1999 | Turngren et al. |
| 5,899,871 | A | 5/1999 | Cartmell et al. |
| 5,935,363 | A | 8/1999 | Gilman et al. |
| 6,004,253 | A | 12/1999 | Riedel et al. |
| 6,043,408 | A | 3/2000 | Geng |
| 6,051,747 | A | 4/2000 | Lindqvist et al. |
| 6,062,285 | A | 5/2000 | Dotta et al. |
| 6,071,267 | A | 6/2000 | Zamierowski |
| 6,087,549 | A | 7/2000 | Flick |
| 6,153,215 | A | 11/2000 | Samuelsen et al. |
| 6,245,960 | B1 | 6/2001 | Eaton |
| 6,284,941 | B1 | 9/2001 | Cox et al. |
| 6,297,420 | B1 * | 10/2001 | Heincke .............. 602/41 |
| 6,313,369 | B1 | 11/2001 | Schiraldi et al. |
| 6,420,622 | B1 | 7/2002 | Johnston et al. |
| 6,512,160 | B1 | 1/2003 | Rutsky |
| 6,520,425 | B1 | 2/2003 | Reneker |
| 6,552,244 | B1 | 4/2003 | Jacques et al. |
| 6,655,112 | B1 | 12/2003 | Cremer et al. |
| 6,662,051 | B1 | 12/2003 | Eraker et al. |
| 6,753,454 | B1 | 6/2004 | Smith et al. |
| 6,765,123 | B2 | 7/2004 | de Jong et al. |
| 6,787,682 | B2 | 9/2004 | Gilman |
| 6,967,261 | B1 | 11/2005 | Soerens et al. |
| 7,105,058 | B1 | 9/2006 | Sinyagin |
| 7,347,846 | B2 | 3/2008 | Hermansson et al. |
| 2001/0000795 | A1 | 5/2001 | Bolian, II et al. |
| 2001/0003148 | A1 | 6/2001 | Coffee |
| 2002/0062097 | A1 | 5/2002 | Simpson |
| 2002/0133502 | A1 | 9/2002 | Rosenthal et al. |
| 2003/0050794 | A1 | 3/2003 | Keck |
| 2003/0233101 | A1 | 12/2003 | Lubock et al. |
| 2004/0015115 | A1 | 1/2004 | Sinyagin |
| 2004/0059199 | A1 | 3/2004 | Thomas et al. |
| 2004/0167456 | A1 | 8/2004 | Kingsford et al. |
| 2005/0149259 | A1 * | 7/2005 | Cherveny et al. ............. 701/208 |
| 2005/0182347 | A1 | 8/2005 | Bishop et al. |
| 2006/0020235 | A1 | 1/2006 | Siniaguine |
| 2006/0034816 | A1 | 2/2006 | Davis et al. |
| 2007/0118096 | A1 | 5/2007 | Smith et al. |
| 2007/0204691 | A1 | 9/2007 | Bogner et al. |
| 2007/0207688 | A1 | 9/2007 | Rasor |
| 2007/0237812 | A1 | 10/2007 | Patel et al. |
| 2008/0004904 | A1 | 1/2008 | Tran |
| 2008/0051688 | A1 | 2/2008 | Lowe |
| 2008/0077091 | A1 | 3/2008 | Mulligan |
| 2008/0108923 | A1 | 5/2008 | Sinyagin |
| 2008/0108927 | A1 | 5/2008 | Sinyagin |
| 2008/0167594 | A1 | 7/2008 | Siniaguine |
| 2008/0234618 | A1 | 9/2008 | Baldock |
| 2009/0024067 | A1 | 1/2009 | Siniaguine |
| 2009/0037224 | A1 | 2/2009 | Raduchel |
| 2009/0131825 | A1 | 5/2009 | Burbank et al. |
| 2009/0216553 | A1 * | 8/2009 | Cellura ............. 705/2 |
| 2009/0245603 | A1 | 10/2009 | Koruga et al. |
| 2010/0114256 | A1 | 5/2010 | Chan et al. |
| 2010/0219546 | A1 * | 9/2010 | Puttler et al. .............. 264/16 |

OTHER PUBLICATIONS

"IMPAC Introduces Comprehensive Cancer Outcomes Analytical Suites" Business Wire (published on Tuesday, Mar. 7, 2000). From Dialog (File 610 Business Wire). Dialog ID No. 00210331.*

"Wound Dressing Update" by Carolina Weller et al.; Journal of Pharmacy Practice and Research, vol. 36, No. 4, 2006.*

Siniaguine, O., "Automatic System for On-Demand Fabrication of Wound Dressings," 2007, pp. 1-15.

International Search Report, PCT/US03/14574, mailing date Oct. 1, 2003.

PCT International Search Report and Written Opinion, PCT/US2009/048412, Oct. 13, 2009, 13 pages.

PCT International Search Report and Written Opinion, PCT/US2008/50762. Jun. 25, 2008, 10 pages.

PCT International Search Report and Written Opinion, PCT/US2005/25362, Sep. 1, 2006, 9 pages.

United States Office Action, U.S. Appl. No. 10/431,888, Aug. 17, 2009, 17 pages.

United States Office Action, U.S. Appl. No. 10/431,888, Jun. 23, 2009, 14 pages.

United States Office Action, U.S. Appl. No. 10/431,888, Nov. 25, 2008, 11 pages.

United States Office Action, U.S. Appl. No. 10/431,888, Dec. 11, 2007, 8 pages.

United States Office Action, U.S. Appl. No. 10/431,888, Apr. 10, 2007, 7 pages.

United States Office Action, U.S. Appl. No. 11/972,854, Feb. 2, 2010, 14 pages.

United States Office Action, U.S. Appl. No. 11/972,854, Jun. 24, 2009, 8 pages.

United States Office Action, U.S. Appl. No. 11/972,846, Jan. 25, 2010, 12 pages.

United States Office Action, U.S. Appl. No. 11/972,846, Jun. 24, 2009, 8 pages.

United States Office Action, U.S. Appl. No. 12/198,604, Jan. 21, 2010, 30 pages.

United States Office Action, U.S. Appl. No. 12/198,604, Jun. 25, 2009, 12 pages.

United States Office Action, U.S. Appl. No. 12/198,676, Sep. 16, 2009, 8 pages.

United States Office Action, U.S. Appl. No. 11/183,459, May 9, 2008, 9 pages.

United States Office Action, U.S. Appl. No. 10/382,422, May 2, 2005, 16 pages.

U.S. Appl. No. 12/164,451, filed Jun. 30, 2008, Siniaguine.

U.S. Appl. No. 12/196,908, filed Aug. 22, 2008, Siniaguine.

U.S. Appl. No. 12/198,604, filed Aug. 26, 2008, Siniaguine.

U.S. Appl. No. 12/198,676, filed Aug. 26, 2008, Siniaguine.

U.S. Appl. No. 11/183,459, filed Jul. 8, 2005, Siniaguine.

U.S. Appl. No. 12/436,071, filed May 5, 2009, Siniaguine.

U.S. Appl. No. 10/431,058.

PCT International Search Report and Written Opinion, PCT/US2010/031912, Jun. 18, 2010, 13 pages.

Canadian Examination Report, Canadian Application No. 2,524,934, Feb. 8, 2010, 3 pages.

European Examination Report, European Application No. 03728787.7, Feb. 26, 2010, 4 pages.

International Search Report and Written Opinion, PCT/US2009/054458, Oct. 9, 2009, 3 pages.

United States Office Action, U.S. Appl. No. 12/198,676, Mar. 12, 2010, 7 pages.

U.S. Appl. No. 10/431,888, filed May 7, 2003, Sinyagin.

U.S. Appl. No. 11/972,854, filed Jan. 11, 2008, Sinyagin.

U.S. Appl. No. 11/972,846, filed Jan. 11, 2008, Sinyagin.

U.S. Appl. No. 10/382,422, filed Mar. 5, 2003, Sinyagin.

U.S. Appl. No. 11/972,452, filed Jan. 10, 2008, Siniaguine.

U.S. Appl. No. 12/110,228, filed Apr. 25, 2008, DeGheest et al.

U.S. Appl. No. 12/436,071, filed May 5, 2009, Siniaguine et al.

PCT International Search Report and Written Opinion, PCT/US2009/039545. May 29, 2009, 12 pages.

European Search Report, EP 03 72 8787, dated May 24, 2006, 4 pages.

Examination Report of the European Patent Office, EP 03 72 8787, dated May 18, 2007, 7 pages.

U.S. Office Action, U.S. Appl. No. 10/431,888, Aug. 17, 2009, 17 pages.

U.S. Office Action, U.S. Appl. No. 10/431,888, Jun. 23, 2009, 14 pages.

U.S. Office Action, U.S. Appl. No. 10/431,888, Nov. 25, 2008, 11 pages.

U.S. Office Action, U.S. Appl. No. 10/431,888, Dec. 11, 2007, 8 pages.

U.S. Office Action, U.S. Appl. No. 10/431,888, Apr. 10, 2007, 7 pages.

European Examination Report, European Application No. 03728787.7, Nov. 15, 2010, 6 pages.
United States Office Action, U.S. Appl. No. 10/431,888, Jun. 10, 2010, 18 pages.
United States Office Action, U.S. Appl. No. 12/436,071, Oct. 22, 2010, 18 pages.
United States Office Action, U.S. Appl. No. 11/972,452, Dec. 3, 2010, 9 pages.
United States Office Action, U.S. Appl. No. 12/198,676, Jan. 19, 2011, 8 pages.
"IMPAC Introduces Comprehensive Cancer Outcomes Analytical Suites," Business Wire, published Mar. 7, 2000. Dialog, (File 610 Business Wire), Dialog ID No. 00210331.
United States Office Action, U.S. Appl. No. 12/436,071, Apr. 1, 2011, 20 pages.
United States Office Action, U.S. Appl. No. 12/198,676, May 13, 2011, 8 pages.
United States Office Action, U.S. Appl. No. 11/972,452, Jun. 14, 2011, 7 pages.
United States Office Action, U.S. Appl. No. 11/972,452, Jul. 28, 2011, 6 pages.
United States Office Action, U.S. Appl. No. 12/436071, Aug. 24, 2011, 19 pages.
United States Office Action, U.S. Appl. No. 12/198,676, Sep. 6, 2011, 8 pages.
U.S. Appl. No. 60/840,412, filed Aug. 28, 2006, Lowe, 6 pages.
United States Office Action, U.S. Appl. No. 11/972,452, Nov. 10, 2011, 6 pages.
United States Office Action, U.S. Appl. No. 12/164,451, Oct. 13, 2011, 17 pages.
United States Office Action, U.S. Appl. No. 12/196,908, Sep. 30, 2011, 7 pages.
Canadian Office Action, Canadian Application No. 2,573,833, May 22, 2012, 4 pages.
United States Office Action, U.S. Appl. No. 12/436,071, Jun. 6, 2012, 20 pages.
Weller, C. et al., "Wound Dressing Update," Journal of Pharmacy Practice and Research, 2006, pp. 318-324, vol. 36, No. 4.
European Examination Report, European Application No. 05773145.7, Jan. 17, 2012, 5 pages.
United States Office Action, U.S. Appl. No. 12/436,071, Feb. 13, 2012, 18 pages.
United States Office Action, U.S. Appl. No. 13/052,553, Mar. 20, 2012, 9 pages.
European Examination Report, European Application No. 03728787.7, Sep. 20, 2012, 11 pages.
United States Office Action, U.S. Appl. No. 13/052,553, Aug. 27, 2012, 11 pages.

* cited by examiner

WOUND CARE TREATMENT SERVICE USING AUTOMATIC WOUND DRESSING FABRICATOR

RELATED APPLICATIONS

This application is a continuation-in-part application of, and claims priority under 35 U.S.C. §120 from, co-pending patent application Ser. No. 10/431,888 entitled "Method for Treating Wound, Dressing for Use Therewith and Apparatus and System for Fabricating Dressing," filed on May 7, 2003, which claims priority to U.S. provisional patent application No. 60/378,635 filed on May 7, 2002, which are incorporated by reference herein in their entirety.

BACKGROUND

1. Field of Art

The present invention generally relates to customizing, fabricating and distributing of wound dressings, and more specifically, to sending specifications associated with customized wound dressings to facilities located remotely from a wound care clinic for fabrication of the wound dressings.

2. Background of the Invention

Currently, the common method of treating wounds is to cover the wounds with wound dressings. Although some wounds may be treated using generic wound dressings, others need customized wound dressings that may include multiple layers of material with different material properties as well as customized shapes and sizes. Typically, a medical practitioner such as a nurse or doctor, first inspects the wound, and then determines based on their personal knowledge, experience, and practice guidelines, the materials, sizes and shapes of wound dressings needed to treat the wound. The practitioner then manually crafts the dressing, first by selecting from an available inventory of standardized dressing supplies, appropriate materials, and then cutting and joining different layers of the materials. The resulting wound dressings are then applied to the wound by the medical practitioners at the wound care clinic. This process thus critically depends on the skill and knowledge of the practitioner as well as what dressing materials happened to be available. If a particular dressing material is not available, then the practitioner must select an alternative, which may be less than satisfactory.

Normally, a patient needs to have the wound dressing replaced on a regular basis, especially for chronic wounds. In order to replace the wound dressings, the patient must either visit the wound care clinic or order components of replacement wound dressings from a wound dressing distributor or a pharmacy. For regulatory reasons, the wound care clinic is prohibited from selling and delivering the wound dressings to patient's home or other facilities where the patient may be residing. Such delivering of the wound dressings is reserved for the wound dressing distributors or other medically related retail outlets. In order to reduce a patient's visits to the wound care clinic, the wound care clinic writes a wound dressing prescription which can be used by the patient in a normal retail setting or can be sent directly to a wound dressing distributor. A conventional prescription only identifies which prepackaged dressing products are to be provided to the patient. The wound dressings are then purchased and/or delivered to the patient's home or a nearby medical facility where the wound dressing may be applied to the wound. In either case, either the patient or a medical practitioner visiting the patent's home must still assemble the final wound dressing from the packaged materials and apply it to the wound. Typical patients may have multiple wounds to be treated and that may require crafting of wound dressings based on different combination of standard wound dressing pre-packaged materials. Due to the differences in skills and abilities among practitioners and patients, this approach may result in inconsistency in how the final wound dressings are crafted and applied, and ultimately, therefore, in the performance of the dressings and how the wounds heal.

The process of picking and organizing kits made out standard size wound dressings at the wound dressing distributors or retail outlets takes up a considerable amount of time because each individual wound dressing needs to be crafted manually by human operators in the patient's home. After receiving orders, the wound dressing distributor organize and sends to the patients or the medical facility a kit of standard wound dressings that typically lasts thirty (30) days, using the same set of materials. However, as the wound condition changes during the healing process that may take several months, the provided wound dressings may become inappropriate for the wound. Therefore, it is preferable to prepare and send the wound dressings to the patients in a smaller batch so that the wound dressings can be adjusted with progress of the wound condition. The prolonged time for receiving orders and preparing the wound dressings, however, makes it difficult for the dressing distributors to prepare and send smaller batches of wound dressings to the patients or the medical facility.

The prepared kit of standard wound dressing materials may not be suitable for the patients for a number of reasons. These flawed wound dressings may result from (i) inaccurate matching of the wound dressing materials needed as the wound healing progresses, (ii) inappropriate designing of the wound dressings based on existing standard packaging, and (iii) non-compliant preparation of the patient's wound dressing based on the kit of standard packaging sent to the patient. Due to these reasons, it is estimated that up to 80% of the patient's wound dressings using conventional wound treatment system and method are flawed or inappropriate for the wounds at the specific time of treatment. Flawed wound dressings may adversely affect the wound healing process and prolong the wound treatment.

SUMMARY

Embodiments provide a method and/or a system for providing wound treatment services to patients by sending wound dressing specifications from a wound care clinic or other medical treatment facilities or entities to remotely located dressing fabrication and distribution facilities. The dressing fabrication and distribution facilities have automatic wound dressing fabricators that fabricate customized wound dressings according to the received wound dressing specifications.

Each wound dressing specification represents a configuration of the wound dressing customized for a specific wound of specific patient. The wound dressing specifications may describe the number, shape, and types of layers of dressing materials as well as additional properties such as protective layer configuration, fluids to be applied to layers, and adjuvants to be applied to the layers, and information about variations to be made in each wound dressing.

The customized wound dressings are fabricated at the dressing fabrication and distribution facilities on the basis of the wound dressing specification and delivered to facilities or the patients' addresses where the customized wound dressings may be applied.

In one embodiment, the wound dressing specifications are sent to an electronic medical information system. The electronic medical information system may receive information on progress of the wound conditions. Information on the progress of the wound conditions associated with the wound dressing specification may be accumulated and analyzed to generate a statistical model of the relationship between wound dressings and wound healing. The statistical model may be referenced to formulate protocols for improved selection of wound dressing.

In one embodiment, the wound dressing specifications are generated after receiving inputs regarding characteristics of the wound from medical practitioner or diagnostic devices and analyzing the inputs by a computer-executed dressing configuration algorithm. The configuration algorithm implements or embodies wound treatment guidance or protocols as developed or used by expert medical practitioners. The configuration algorithm implements an expert system that guides inexperienced medical practitioners as well as experienced medical practitioners to design wound dressings appropriate for the wounds of the patients according to clinically established protocols. The practitioner may input the wound characteristics into a data entry system, which may include a dedicated automatic wound dressing fabricator where the practitioner is located, a web-based application interface, or a handheld data entry device specifically configured for such data entry of wound characteristics.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

Figure 1A:
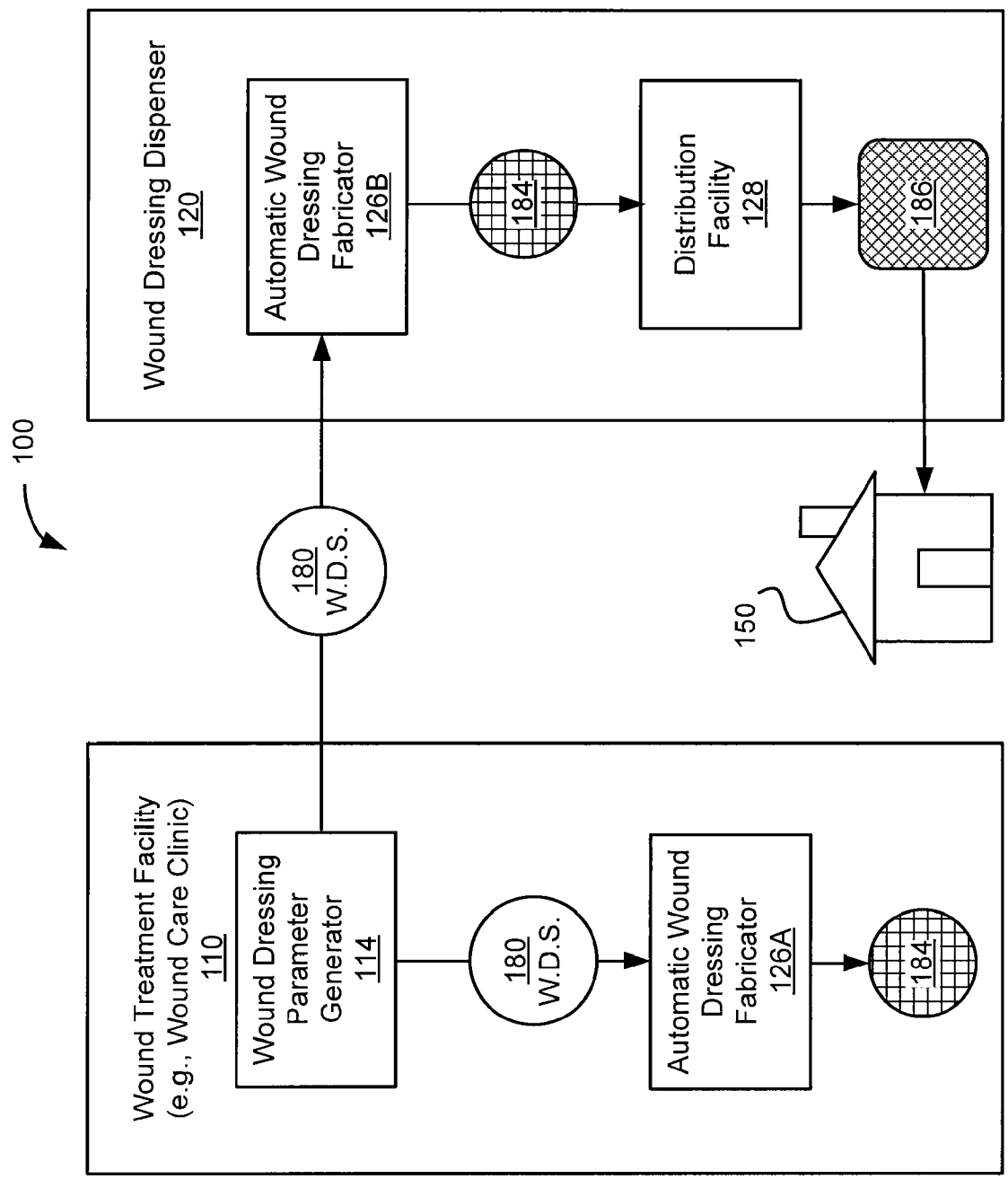
FIG. 1A is a functional block diagram illustrating a wound treatment system where wounds are diagnosed at a wound treatment facility and wound dressings are delivered to patients from a wound dressing dispenser, in accordance with one embodiment.

The figures depict embodiments of the present invention for purposes of illustration only. One skilled in the art will readily recognize from the following description that alternative embodiments of the structures and methods illustrated herein may be employed without departing from the principles of the invention described herein.

DETAILED DESCRIPTION

Embodiments provide a method and/or system allowing patients to receive consistent, effective and convenient wound care by allowing medical practitioners to order prescriptions for customized dressings, having the prescription sent electronically so that customized wound dressings are fabricated at a remote wound dressing dispenser and sent to a predetermined location where the wound dressings can be applied. The wound dressing dispenser is equipped with one or more automatic wound dressing fabricators to fabricate wound dressings according to wound dressing specifications. The wound dressing specifications are generated with the aid of a computer-based configuration algorithm that recommends the configuration of wound dressings based on inputs regarding wound characteristics. Each wound dressing is customized to, and fabricated for, the particular characteristics of a patient's wound. The generated wound dressing specifications are confirmed into an electronic prescription by a medical practitioner such as a doctor or a nurse before being communicated between the medical facilities to provide consistent and appropriate wound dressings without duplicative diagnosis of the wound. Further, telemedicine for wound care may be implemented by having a medical practitioner diagnose a patient's wounds remotely, provide the wound dressing specification to the wound dressing dispenser for fabrication, having the wound dressing dispenser fabricate the wound dressing, and having the wound dressing dispenser send the fabricated wound dressing to the patient. Because the wound dressings are systematically created by the configuration algorithm based upon diagnosis by a medical practitioner as the healing progresses, the patients receive relevant treatments for their wounds. Further, wound treatment outcomes may be collected to develop improved evidence-based medicine treatment protocols.

System Architecture of Distribution of Wound Dressing

Patients, particularly in suburban and rural area, typically live remote from wound care clinics and it is often inconvenient for the patients to visit the wound care clinic to receive an initial wound dressing or replace an existing wound dressing. Therefore, after a patient receives a customized wound dressing at a wound care clinic, the patient may prefer to have the customized wound dressings delivered to the patient's residence or a nearby medical facility (e.g., home health visiting nurses agencies). The wound care clinics, however, are very restricted from selling or mailing the wound dressings to the patients under federal or state regulations such as the Medicare anti-fraud statutes and Stark Law. In embodiments described below with reference to FIGS. 1A and 1B, a patient's wounds are diagnosed at a wound treatment facility but the wound dressings other than the first wound dressings are fabricated at a wound dressing dispenser and delivered to the patient's residence or nearby medical facility. In this way, the patient conveniently receives high-quality, customized wound treatment while complying with the regulatory restrictions.

FIG. 1A is a functional block diagram illustrating a wound treatment system 100 where wounds are diagnosed at a wound treatment facility 110 and wound dressings are delivered to patients from a wound dressing dispenser 120, in accordance with one embodiment. The wound treatment facility 110 (e.g., wound care clinic) receives the patients and medical practitioners at the facility to diagnose wound conditions of the patients. Customized wound dressings 184 are fabricated based on such specifications 180 at the wound treatment facility 110 using the automatic wound dressing fabricator 126A. After a doctor or other authorized medical professionals approve the wound dressing specifications 180, the wound dressing specifications 180 are sent to the wound dressing dispenser 120 located remotely from the wound treatment facility 110. The wound dressing dispenser 120 fabricates wound dressings 184 and sends the wound dressings 184 to the distribution facility 128 where the fabricated wound dressings are packed into packages 186 and sent to a predetermined location 150. The predetermined location 150 may be, among others, the patient's residence, a nearby medical facility, an office of medical practitioners visiting the patients, and long term care facilities.

The wound treatment facility 110 and the wound dressing dispenser 120 are remotely located. The term 'remotely' is used herein broadly to include cases where the wound dressing facility 110 and the wound dressing dispenser 120 are located in the same building but in different rooms as well as cases where the wound dressing facility 110 and the wound dressing dispenser 120 are located in different cities or countries The wound treatment facility 110 is equipped with, among other devices, a wound dressing parameter generator 114, as described below in detail with reference to FIG. 2. The wound dressing parameter generator 114 receives inputs from medical practitioners (e.g., physicians or nurses) as described, for example, in U.S. patent application Ser. No. 10/431,888 entitled "Method for Treating Wound, Dressing for Use Therewith and Apparatus and System for Fabricating Dressing," filed on May 7, 2003, which is incorporated by reference herein in its entirety. The wound dressing parameter generator 114 may also receive diagnostic information from stationary or portable diagnosing devices such as digital imaging devices.

The inputs or diagnostic information provided to the wound dressing parameter generator 114, for example, include wound characteristics such as the type of wound, the amount of exudates, the type of exudates, the color of exudates, the odor of exudates, dimension (width, lengths, depth) of the wound, the shape of the wound, tunneling of the wound, base color of the wound, the condition of wound edges, amount of necrosis, advancement level, bacterial colonization, epithelialization, sensitivity, severity, health of surrounding skin, periwound properties, pain level, induration, and granulation. The wound types may include, for example, burn, cut, ulcer and abrasion. The exudates may include, for example, none, low, medium and heavy. The characteristics of the wounds may also be captured by a digital camera or various types of two- or three-dimensional scanners. The wound dressing parameter generator 114 generates the wound dressing specification, as described below in detail with reference to FIG. 2.

Preferably, the wound treatment facility 110 also has an automatic wound dressing fabricator 126A. The wound dressing fabricator 126A receives the wound dressing specification 180 and automatically fabricates the wound dressings, for example, as disclosed in U.S. patent application Ser. No. 10/431,888 entitled "Method for Treating Wound, Dressing for Use Therewith and Apparatus and System for Fabricating Dressing," filed on May 7, 2003, which is incorporated by reference herein in its entirety. The wound dressings fabricated from the wound dressing fabricator 126A are applied to the wounds of the patients while the patient visits the wound treatment facility 110 for diagnosis and treatment. The replacement wound dressings between the visits to the wound treatment facility 110 may be fabricated and delivered by the wound dressing dispenser 120 to the predetermined location 150.

In some cases, the wound treatment facility 110 is not equipped with the automatic wound dressing fabricator 126A. In such embodiments, the wound treatment facility 110 would include the wound dressing parameter generator 114, as described above, for receiving the wound characteristics inputs. In such cases, all of the customized wound dressings are ordered and received from the wound dressing dispenser 120.

The wound dressing dispenser 120 includes, among other components, an automatic wound dressing fabricator 126B and a distribution facility 128. The automatic wound dressing fabricators 126A, 126B are also referred to as the "wound dressing fabricator 126" herein. The automatic wound dressing fabricator 126B is essentially the same as the automatic wound dressing fabricator 126A but may be configured for fabrication or processing a large numbers of wound dressings. The fabricated wound dressings 184 are then passed over to the distribution facility 128 where the fabricated wound dressings 184 are packed into packages 186 for delivery to the predetermined location 150. The packages 186 may be delivered to the predetermined location 150 by conventional shipping methods, by patients' pickup at the distribution facility 128, or by medical practitioner visiting the patient to apply the fabricated wound dressings.

The wound dressing specification 180 may be communicated between the wound treatment facility 110 and the wound dressing dispenser 120 via various communication networks or storage media. Preferably, the wound dressing specification 180 is sent as an encoded data file via a communications network, which includes the Internet, alone or in combination with a cellular phone network, a public switched telephone network (PSTN), and a satellite telecommunications network (STN). The wound dressing specification 180 may be sent, for example, in emails, by faxes, by internet web-based requests. The wound dressing specification 180 may also be sent via a tangible storage medium such as a floppy disk, a USB (Universal Serial Bus) flash memory, or a smart card.

Figure 1B:
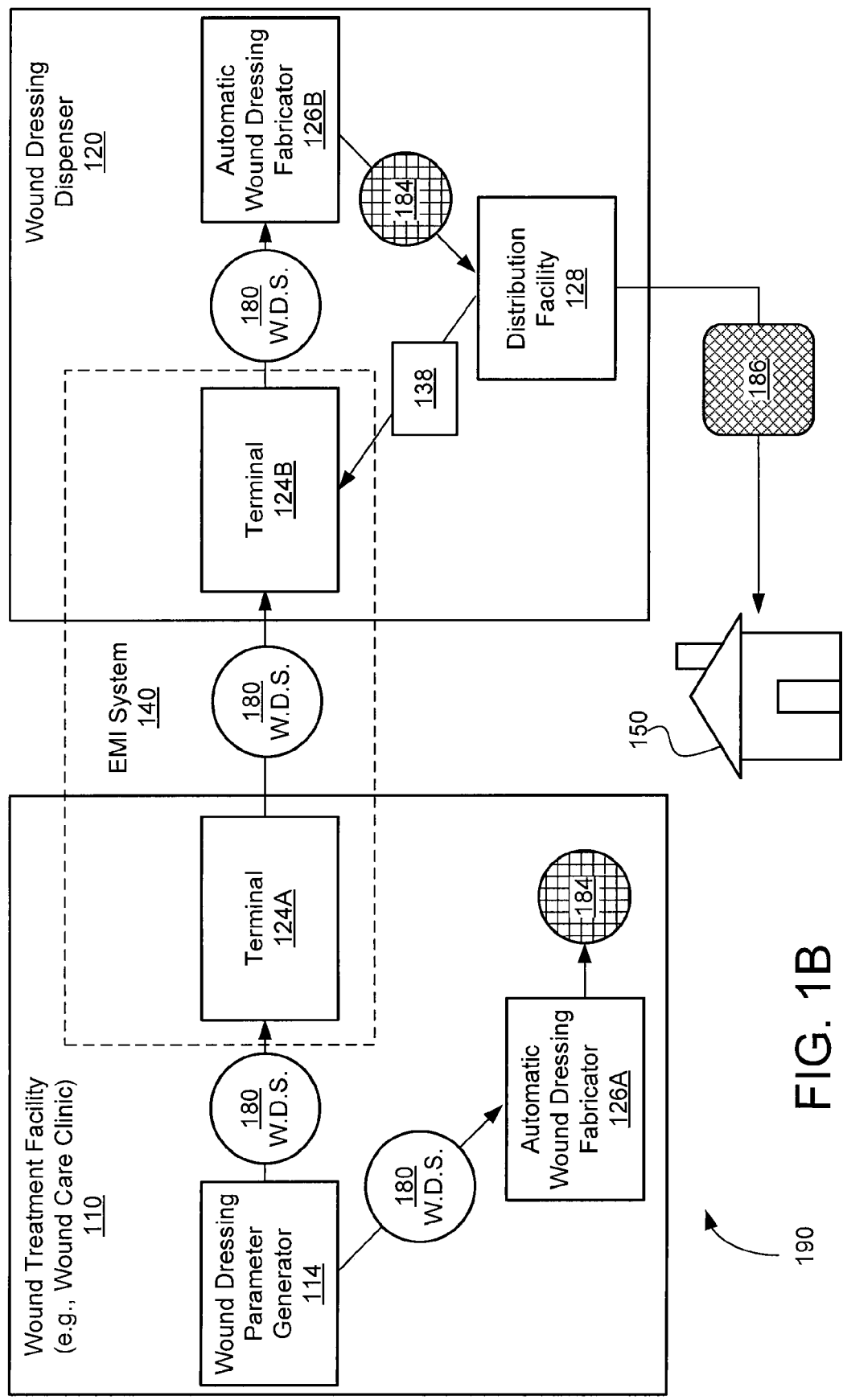
FIG. 1B is a functional block diagram illustrating a wound treatment system including an electronic medical information system between a wound treatment facility and a wound dressing dispenser, according to one embodiment.

FIG. 1B is a functional block diagram illustrating a wound treatment system 190 including an electronic medical information system 140 between a wound treatment facility 110 and a wound dressing dispenser 120, according to one embodiment. In addition to the components of the wound treatment system 100 of FIG. 1A, the wound treatment system 190 of FIG. 1B further includes an electronic medical information system 140 having multiple terminals 124A, 124B deployed across multiple medical facilities. The wound dressing parameter generator 114, automatic wound dressing fabricators 126A, 126B, and the distribution facility 128 are essentially the same as described above with respect to FIG. 1A except that (i) the wound dressing parameter generator 114 and the automatic wound dressing fabricator 126B communicate via the electronic medical information system 140, (ii) the distribution facility 128 provides update information 138 on the dispatch status of the ordered wound dressings, and (iii) a configuration algorithm is updated by the electronic medical information system 140, as described below in detail with reference to FIG. 2.

The electronic medical information system 140 stores patient information, insurance information, and other medical information, as described below in detail with reference to FIG. 3. The electronic medical information system 140 may be accessed by the wound treatment facility 110, the wound dressing dispenser 120 and the patients, among other purposes, to obtain medical records of the patients, to obtain approval or authentication from medical practitioners, to send the wound dressing specifications, to update the order status of the wound dressings, to track the order of the wound dressings, and to process reimbursement for the wound dressings from insurance companies.

The electronic medical information system 140 may be deployed or integrated with existing medical information systems in various medical facilities and insurance companies to share medical records and to provide integrated medical services to the patients. For example, the medical information systems provided by EpicCare and EpicWeb from Epic Systems Corporation of Verona, Wis. may be used as the electronic medical information system 140. In other cases, the electronic medical information system 140 is operated and maintained by one medical facility.

Figure 3:
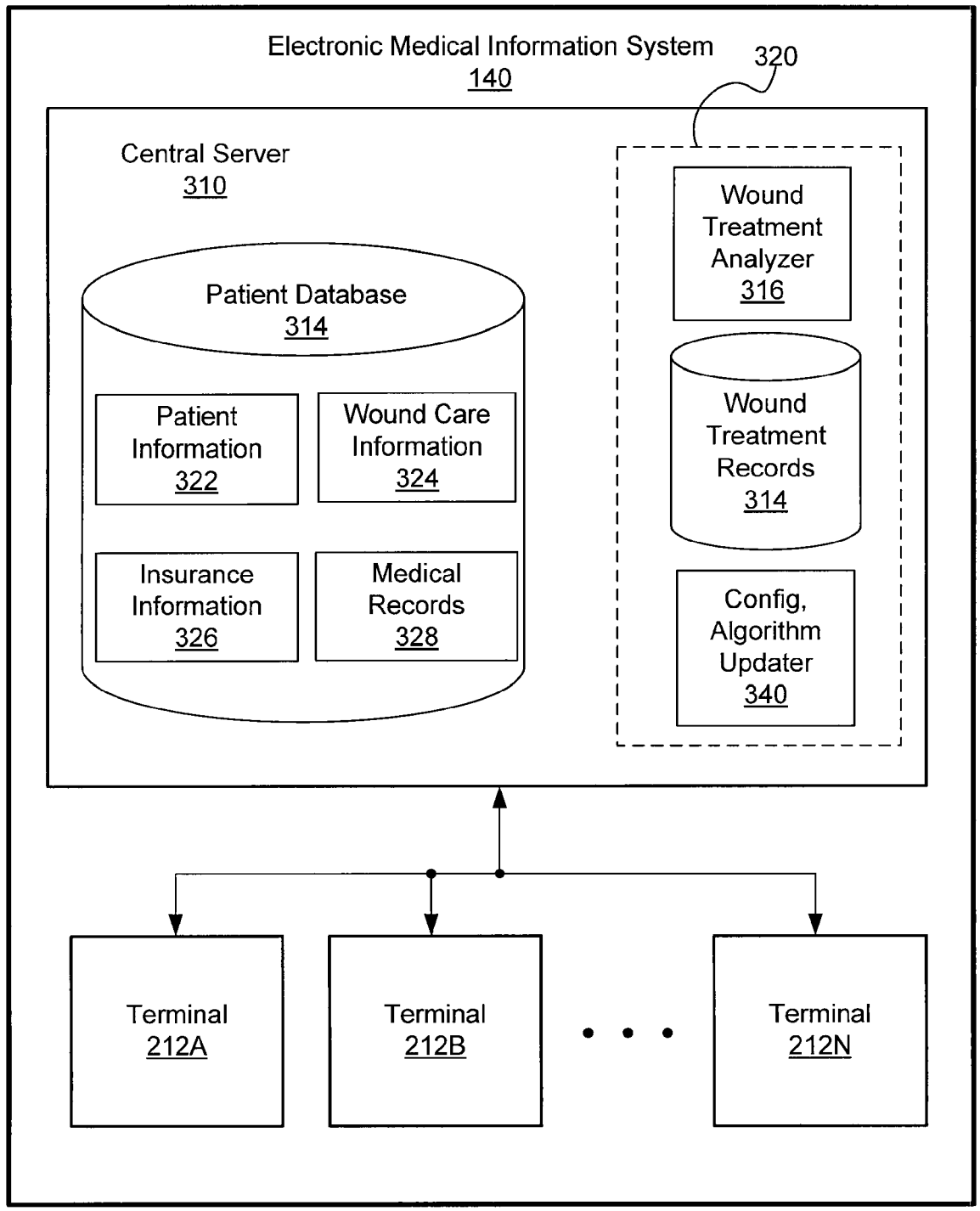
FIG. 3 is a block diagram of an electronic medical information system according to one embodiment.

The advantages of using the electronic medical information system 140 for the wound treatment system 190 include, among others, (i) integrated wound treatment service from multiple medical facilities, (ii) constant updating of the wound dressing order status and other medical information to the patients (when the patients are allowed to access the electronic medical information system), and (iii) accumulation and analyzing of the wound treatment information to formulate improved wound treatment protocols, as described below in detail with reference to FIG. 3.

There may be additional events between the transmittal of the wound dressing specifications 180 at the terminal 124A and receiving of the wound dressing specifications 180 at the terminal 124B. Before the electronic medical information system 140 passes the wound dressing specification 180 to the automatic wound dressing fabricator 126B, the electronic medical information system 140 may, for example, perform the following operations: (i) verify the patient information, (ii) confirm insurance coverage associated with the wound dressings, (iii) request reimbursement from insurance company, (iv) receive approval or authorization from one or more medical practitioners for using the customized wound dressings on the patients as specified by the wound dressing specifications, and (v) inform the prescribing or referring physicians about the wound care treatment status of their patients being treated remotely (e.g., at home health agencies or long term care facilities). In other cases, the wound dressing specifications 180 are relayed between the terminals 124A, 124B without other intervening events.

Architecture of Wound Dressing Parameter Generator

Figure 2:
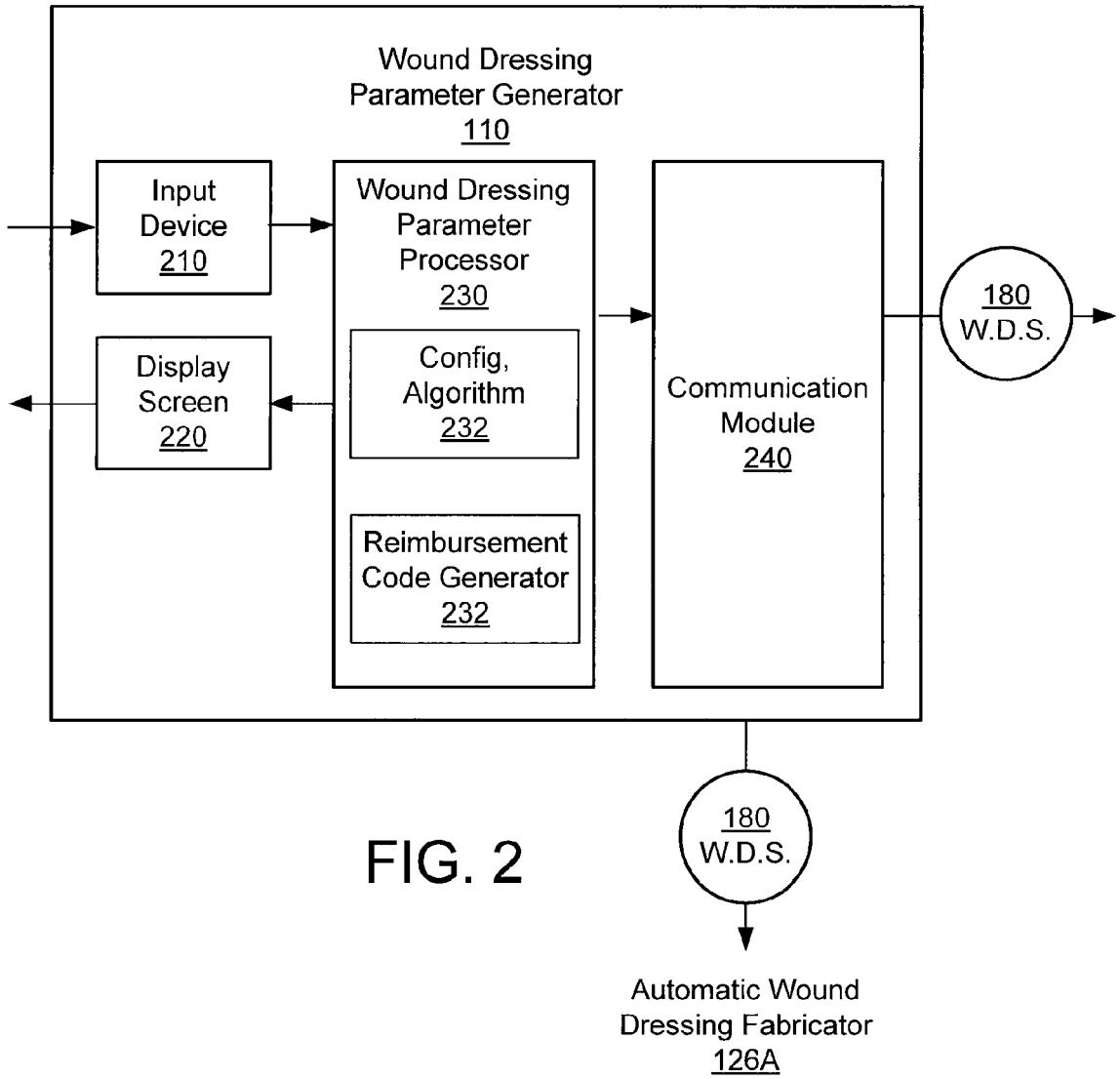
FIG. 2 is a block diagram of a wound dressing parameter generator according to one embodiment.

FIG. 2 is a block diagram illustrating the wound dressing parameter generator 110 according to one embodiment. The wound dressing parameter generator 110 receives inputs from the medical practitioners or other diagnosing devices to generate the wound dressing specifications indicating the configuration of customized wound dressings. The wound dressing parameter generator 110 includes, among other components, an input device 210, a display screen 220, a wound dressing parameter processor 230, and a communication module 240. One or more of these components, in conjunction with other components, may be implemented in the form of hardware, firmware, software, or any combinations thereof.

The input device 210 receives inputs from the medical practitioners diagnosing the wounds. The input device 210 may include, among other devices, keypads, touchscreens, mouse or other conventional input devices to receive inputs from the medical practitioners. The input device 210 may also include other sensor devices such as a digital camera or various types of two- or three-dimensional scanners.

The display screen 220 displays the user inputs and other wound related information to the medical practitioners for verification. Preferably, the display screen 220 operates in conjunction with the input device 210 and the wound dressing parameter processor 230 to display a list of available options for designing the wound dressings. The display screen 220 may be implemented as any conventional display devices.

The wound dressing parameter processor 230 receives the wound characteristics from the input device 210 to generate the wound dressing specifications. The wound dressing parameter processor 230 includes a configuration algorithm 232 that automatically selects or recommends wound dressing configurations. Preferably, the configuration algorithm 232 implements a decision tree that guides medical practitioners to choose and navigate through a set of design choices for the wound dressing in an organized and efficient manner. The configuration algorithm 232 may implement an expert system that assists in the designing and determining the configuration of the wound dressings in accordance with wound treatment guidance or protocols as developed or employed by expert medical practitioners. The configuration algorithm 232 may be developed using various guidelines and protocols available from various sources including, among others, Carrie Sussman et al., "Wound Care: A Collaborative Practice Manual," Lippincott Williams & Wilkins (2007); Carol Dealey "The Care of Wounds: A Guide for Nurses," Blackwell Publishing (1999); Sharon Baranoski et al., "Wound Care Essentials: Practice Principles," Lippincott Williams & Wilkins (2007); and Cathy Thomas Hess, "Skin & Would Care: Skin and Wound Care," Lippincott Williams & Wilkins (2007), which are incorporated by reference herein in their entirety.

The configuration algorithm 232 may also operate in more than one mode, each mode allowing medical practitioners with different levels of expertise to configure the wound dressing. For example, in a first mode, the configuration algorithm 232 presents a limited number of choices for the basic configuration of the wound dressings. In a second mode, the configuration algorithm 232 presents more number of choices for the advanced configuration of the wound dressings. The first mode may be selected for use by semi-skilled practitioners (e.g., technicians), while the second mode may be selected for use by expert users (e.g., nurses, doctors).

The wound dressing parameter processor 230 may also function as a rule-based engine for generating the design of the wound dressing. The wound dressing parameter processor 230 stores wound treatment information received via the input device 210 and/or the electronic medical information system 140. The wound treatment information may include, among others, previous wound dressings provided to a patient, previous treatment outcomes for other patients with similar wounds, medications taken by the patient, and medical conditions of the patients. The wound dressing parameter processor 230 may then be analyzed to recommend a suitable wound dressing for a patient. The wound dressing parameter processor 230 may operate in conjunction with the electronic medical information system 140 to analyze the wound treatment information and/or recommend the wound dressing. One or more parameters for the configuration algorithm 232 may also be received at the wound dressing parameter generator 110 to customize clinical protocols of the medical practitioners in the medical facility where the wound dressing parameter generator 110 is installed.

Alternatively, the configuration algorithm 232 may not be stored on the wound dressing parameter generator 110. Instead, the configuration algorithm 232 is stored in a central server that communicates with the wound dressing parameter generator 110. The wound dressing parameter processor 230 may remotely access the configuration algorithm stored in such central server when wound dressing specifications 180 need to be generated. Storing the configuration algorithm 232 in the remote server is advantageous, among other reasons, because (i) the configuration algorithm 232 may be maintained as a trade secret, and (ii) the configuration algorithm 232 can be quickly and easily updated without having to individually update numerous remotely located wound dressing parameter generators 110.

The wound dressing parameter processor 230 may also include reimbursement code generator 232 for generating reimbursement codes that is used for requesting reimbursement from insurance company, Medicare, or other reimbursing entities. The reimbursement codes may, for example, be codes for HCPCS (Healthcare Common Procedure Coding System) from Medicare. The reimbursement code generator 232 may be implemented, for example, as a look-up table. The look-up table may be updated via internet or other communications network when changes in the reimbursement codes occur. Preferably, the generated reimbursement codes is sent to the wound dressing dispenser 120 together with the wound dressing specification 180 as part of an electronic wound dressing prescription, as described below in detail with reference to FIG. 5. The wound dressing dispenser 120 may use the reimbursement codes to request reimbursement for expenses associated with the wound dressing to insurance company, Medicare, or other reimbursing entities to collect fees. Alternatively, the reimbursement codes may be generated by the electronic medical information system 140 or the wound dressing dispenser 120.

The communication module 240 allows the wound dressing parameter generator 110 to send the wound dressing specifications to the automatic wound dressing fabricators 126A, 126B via an internal communications interface, a communications network or a computer readable storage medium. The communication module 240 may communicate wirelessly or via a wired network. The communication module 240 also allows the configuration algorithm 232 to be updated based on the update information received from a central server, as described below in detail with reference to FIG. 3. The communication module 240 may be replaced or be used in conjunction with a storage media writer such as a floppy disk, a universal serial bus (USB) terminal or a smart carder reader/writer. The communication module 240 may also send the wound dressing specification to the automatic wound dressing fabricator 126A that is located in the same location or in proximity to the wound dressing parameter generator 110.

The wound dressing parameter generator 110 may be a stand-alone data entry device such as a personal computer or a handheld device (e.g., PDA (Personal Digital Assistant)) that is specialized for generating the wound dressing specification. Alternatively, the wound dressing parameter generator 110 may be a part of, and integrated with another device such as the wound dressing fabricator 126A, as described below in detail with reference to FIG. 4B. The wound dressing parameter generator 110 may also communicate with a server via a web-based application interface to generate the wound dressing specification.

The wound dressing parameter generator 110 may communicate with a portable data entry device (not shown) such as a PDA, a smart phone, or a laptop computer to receive inputs regarding the wound characteristics or other wound treatment information. The medical practitioner may use the portable entry device to conveniently input the wound characteristics and other information to the wound dressing parameter generator 110 without having to walk over to the wound dressing parameter generator 110. The portable data entry device may communicate wirelessly or by wire with the wound dressing parameter generator 110.

Architecture of Electronic Medical Information System

FIG. 3 is a block diagram of the electronic medical information system 140, according to one embodiment. The electronic medical information system 140 provides various information services associated with the wound treatment including, among others, (i) storing of the patient information and insurance information, (ii) tracking the order status of the wound dressings, (iii) accumulating and analyzing of the wound treatment parameters and statistics, (iv) updating of the configuration algorithm 232, (v) verification or assessment of the wound dressing specification by medical practitioners, (vi) processing of financial transactions associated with the wound dressing design and fabrication, (vii) accumulate and analyze types of wound dressings selected or authorized by the medical practitioners for certain types of wounds to benchmark the preferred or optimized wound treatment practices, and (viii) receiving inputs from patients to check whether the patients are complying with treatment plans provided by the medical practitioners. Such additional services are merely illustrative and various other types of services may also be provided by the electronic medical information system 140.

The electronic medical information system 140 of FIG. 4 includes, among other components, a central server 310 and multiple terminals 212A through 212N (hereinafter collectively referred to as terminals 212). As illustrated in FIG. 1B, the terminals 212A through 212N may be deployed in various locations within the same medical facility or in different medical facilities. The terminals 212A through 212N communicate with the central server 310 via a communications network.

The central server 310 may include, among other components, a patient database 314 and a wound information processing module 320. The patient database 314 may store information such as patient information 322, wound care information 324, insurance information 326, and medical records 328.

The patient information 322 includes patient's personal information such as patient's name, gender, address, phone number, date of birth, and age. The patient information 322 may be collected from the wound dressing parameter generator 114, terminals 124A through 124N or other sources including patient medical records in medical facilities.

The wound care information 324 includes current and previous wound dressing specifications, order status of wound dressings, tracking information for the dispatched wound dressings, the wound dressing fabricated for the patient, current and past wound characteristics, progress of wound conditions, and other medical conditions relevant to the wound treatment. Such wound care information may be classified by the location of the wound.

The insurance information 326 includes, among others, the details of the insurance company (e.g., identification, name, address, contract person, and phone number), the insurance policy group number, plan effective date, plan expiration date, plan type (e.g., Medicare, Medicaid, Health Maintenance Organization (HMO), or Preferred-Provider Organization (PPO)), name of the insured, insured's relationship to the patient, and policy number.

The medical records 328 include, among other information, surgical history, obstetric history, medications and medical allergies, family history, immunization history, results of blood tests, x-ray results, biopsy results, results from specialized testing, and diagnosed cause of the medical condition.

The information stored on the patient database 314 is merely illustrative and not limiting. A combination or subset of the above described information may be used. Alternatively, additional information associated with the patients may be stored in the patient database 314.

The central server 310 also includes the wound information processing module 320. The wound information processing module 320 processes information associated with the wound treatment received and accumulated from various sources including the terminals 212, the wound dressing parameter generator 114, and the automatic wound dressing fabricator 126. The wound information processing module 320 may also update the configuration algorithm 232 stored on the wound dressing parameter generator 110.

In an example of the wound information processing module 320 illustrated in FIG. 3, the wound information processing module 320 of FIG. 3 includes, among other components, a wound treatment analyzer 316, wound treatment records 314, and a configuration algorithm updater 340. The wound treatment records 314 store information associated with progress and history of wound treatment for multiple wound patients. The wound treatment records 314 are preferably extracted from the medical records 328 in the patient database 314. The wound treatment analyzer 316 generates statistics on efficacy of the wound treatment or progress of wound conditions for various wound dressing configurations. Specifically, the wound treatment analyzer 316 reads and processes information stored in the wound treatment records 314 to determine factors such as the average time for healing certain types of wounds when certain wound dressings were used, which wound dressings resulted in better healing for a certain type of wound. Demographic information and information on other medical conditions of the wound patients may also be taken into account by the wound treatment analyzer 316 during the statistical analysis.

The data provided by the wound treatment analyzer 316 may be used by an expert to develop an improved treatment protocol for wound treatment. The updated treatment protocol may be used to update the configuration algorithm 232 of the wound dressing parameter generator 110. The configuration algorithm updater 340 may then send the update information to the wound dressing parameter generator 110 and update the configuration algorithm 232 stored therein. Preferably, the updating of the configuration algorithm may be provided only to medical facilities that subscribe to the update service or pay for additional fees for the updated configuration algorithm. The wound treatment analyzer 316 may operate in conjunction with the wound dressing parameter generator 110 to collect the wound treatment information and to generate the protocols for wound treatment.

It should be appreciated that the updated treatment protocols and configuration algorithm can be specifically targeted and adapted for different institutions or care facilities. For example, a large long term care corporation covering thousands of patients, may be interested in developing treatment protocols and a configuration algorithm that is particular to its needs (e.g., minimizing average total cost per wound treatment) while a different healthcare organization, such as a university teaching hospital may use wound treatment records to develop different treatment protocols and configuration algorithm (e.g., a protocol that minimizes the length of time it takes for certain difficult wounds to heal. Such treatment protocols may be used in conjunction with configurable parameters of the wound dressing parameter generators to customize the treatment protocols for a specific medical facility.

The wound information processing module 320 may also be used for assessing efficacy and issues associated with newly developed wound dressing materials. Insufficient data may be available for newly developed wound dressing materials. The wound dressing information processing module 320 may track the treatment records of such new wound dressing materials and reflect the treatment result of the new wound dressing materials in the next updates for the configuration algorithm 232. The wound information processing module 320 may also be used for identifying correlations of medical conditions and predicting progress of wounds based on statistical models. Preferably, such information may be provided to the medical practitioners to help practitioners develop plans associated with the wound treatment.

Such wound information processing module may be provided at the wound dressing parameter generator 114 or the automatic wound dressing fabricator 126 in addition to or as an alternative to the wound information processing module 320 of the electronic medical information system 140. The wound information processing module of the wound dressing parameter generator 114 or the automatic wound dressing fabricator 126 may collect wound treatment information to generate parameters that may be used by the wound dressing parameter generator 114 to generate the wound dressing specification 180 or to modify (or supplement) the configuration of the wound dressing as defined by the wound dressing specification 180 at the automatic wound dressing fabricator 126. Preferably, each wound information processing modules of the wound dressing parameter generator 114 or the automatic wound dressing fabricator 126 manages and implements a wound treatment protocol specific to the facility or the machine while the wound information processing module 320 of the electronic medical information system 140 manages and implements wound treatment protocol that is more general (e.g., a statewide or nationwide protocol).

Architecture of Automatic Wound Dressing Fabricator

Figure 4A:
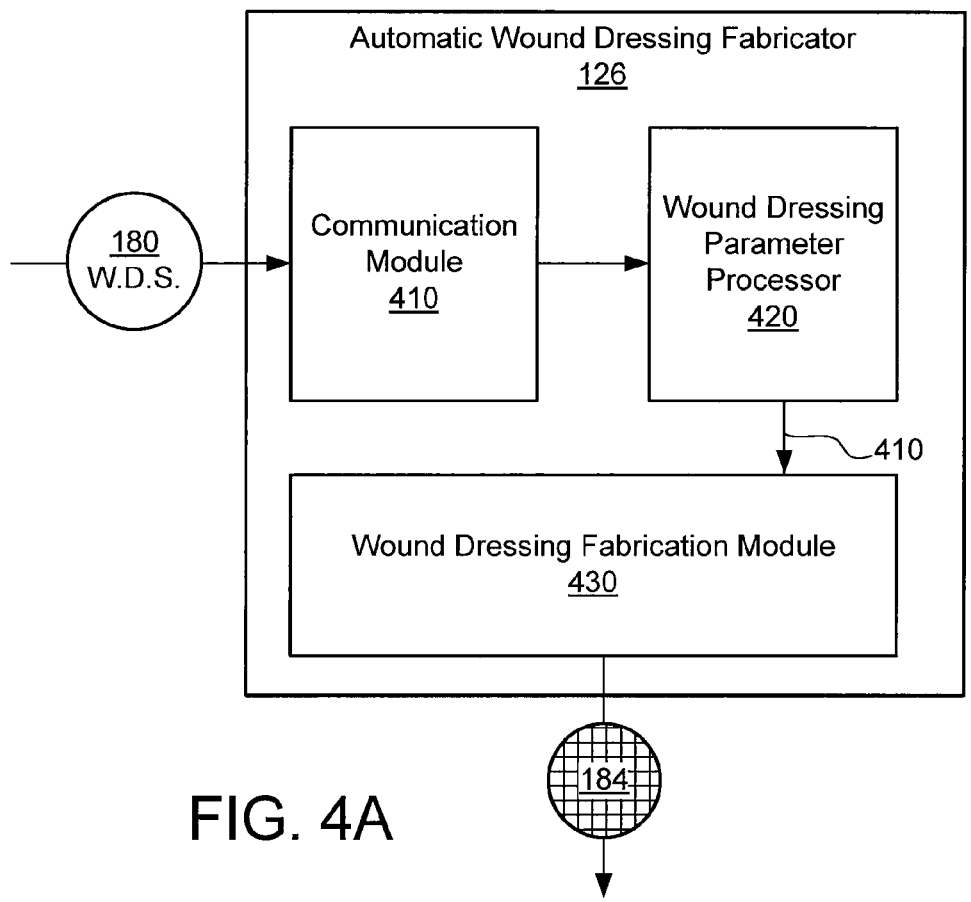
FIG. 4A is a block diagram of an automatic wound dressing fabricator according to one embodiment.

FIG. 4A is a block diagram illustrating an automatic wound dressing fabricator 126, according to one embodiment. The wound dressing fabricator 126, includes among other components, a communication module 410, a wound dressing fabrication processor 420, and a wound dressing fabrication module 430. One or more of the components of the wound dressing fabricator 126, may be implemented as hardware, firmware, software or any combinations thereof. As described below in detail with reference to FIG. 4B, the automatic wound dressing fabricator 126 may be integrated with the wound dressing parameter generator 110. Alternatively, the automatic wound dressing fabricator 126 may be implemented in a hardware device separate from the wound dressing parameter generator 110.

The communication module 410 communicates with one or more wound dressing parameter generators 110 deployed remotely in various medical facilities. As described above with reference to the communication module 240 of FIG. 2, the communication module 410 may also communicate via various networks. Alternatively, the communication module 410 may be substituted with a storage media reader for reading information from a floppy disk, a USB flash-drive, and other memory cards.

The wound dressing fabrication processor 420 is coupled to the communication module 410 to receive the wound dressing specification 180 from the wound dressing parameter generator 110. The wound dressing fabrication processor 420 reads the wound dressing specification 180 and converts that specification into fabrication signals. The fabrication signals control the operation of the actuators in the wound dressing fabrication module 430. The fabrication signals are sent to the wound dressing fabrication module 430 to activate actuators and fabricate wound dressings.

The wound dressing fabricator module 430 includes actuators and control devices for fabricating the wound dressing, for example, as described in U.S. patent application Ser. No. 10/431,888 entitled "Method for Treating Wound, Dressing for Use Therewith and Apparatus and System for Fabricating Dressing," filed on May 7, 2003, which is incorporated by reference herein in its entirety. The wound dressing 184 fabricated at the wound dressing fabrication module 430 may then be provided to the medical practitioner in the wound treatment facility 110 for application to the wound at the wound treatment facility 110 or to the distribution facility 128 for delivery to a predetermined location.

Figure 4B:
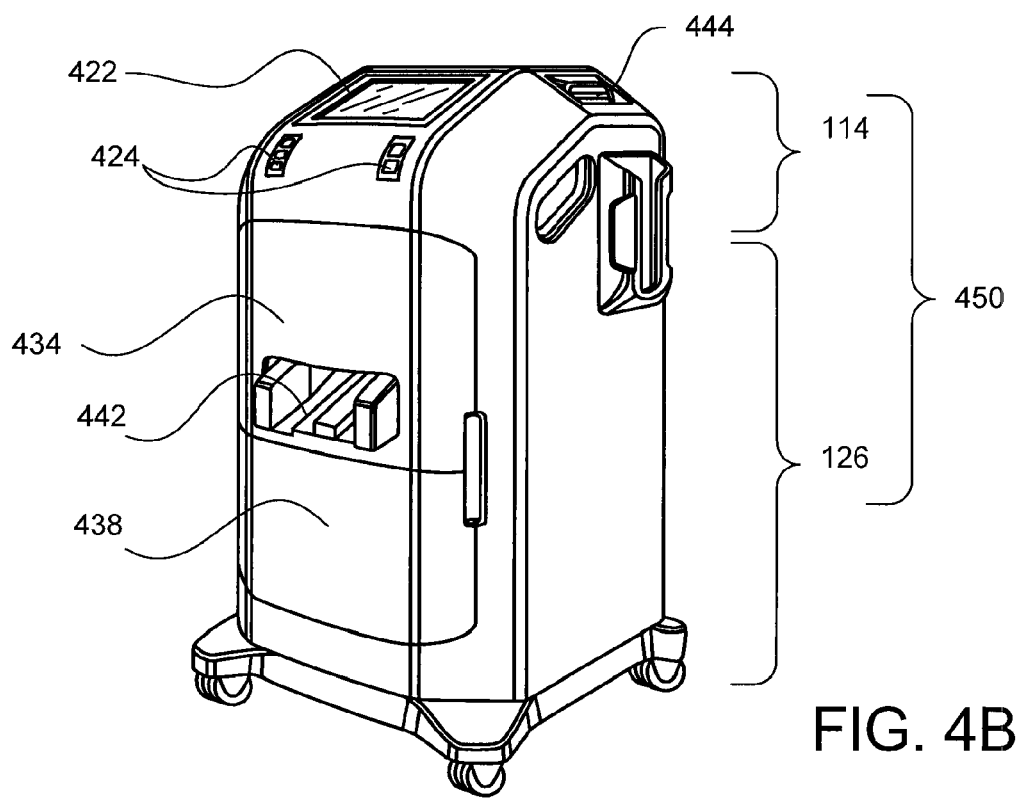
FIG. 4B is a perspective view of an integrated fabricator according to one embodiment.

FIG. 4B is a perspective view of an integrated wound parameter generator-wound dressing fabricator 450 (hereinafter referred to as the "integrated fabricator 450") according to one embodiment. The integrated fabricator 450 includes, among others, components for both the wound dressing parameter generator 114 and the automatic wound dressing fabricator 126. Specifically, the integrated fabricator 450 includes a touch screen 422, switches 424, a communication module (not shown), a connector 444 and a wound dressing parameter processor (not shown) as components of the wound dressing parameter generator 114. The integrated fabricator 450 may receive inputs related to patient information and the wound characteristics via the touch screen 422, switches 424, and a diagnostic device coupled to the connector 444.

The integrated fabricator 450 also includes an actuator assembly 434, a cartridge holder 438, a wound dressing outbox 442, and a controller as the components of the automatic wound dressing fabricator 126. The cartridge holder 438 stores multiple cartridges, each storing materials for fabricating customized wound dressings. The cartridges may be replaced or refilled when the materials stored in the cartridges are depleted. The actuator assembly 434 includes actuators that manipulates, processes, and applies the materials from the cartridges according to the fabrication instructions from the wound dressing parameter processor 420 to fabricate the customized wound dressings. The fabricated wound dressings are discharged through the wound dressing outbox 442.

Preferably, an alert is displayed on the touch screen 422 when the materials left in the cartridges drops below a predetermined level.

The wound dressing parameter generator 114 and the automatic wound dressing fabricator 126 of the integrated fabricator 450 may communicate via an internal bus or an internal communication line (not shown). In other cases, the integrated fabricator 450 includes one or more central processing units (CPUs) and one or more computer readable storage medium storing instructions to be executed by the CPUs. The central processing units (CPUs), in conjunction with the computer readable storage medium, performs the function of both the wound dressing parameter processor 230 of the wound dressing parameter generator 114 and the wound dressing parameter processor 420 of the automatic wound dressing fabricator 126.

The integrated fabricator 450 allows the medical practitioners to access the central server 310 of the electronic medical information system 140. In other words, the integrated fabricator 450 also functions as the terminal 212 of the electronic medical information system 140. The integrated fabricator 450 may also be equipped with a storage media interface device (not shown) for reading or writing wound dressing specification and/or the patient information from or to portable memory storage media such as a floppy disk, a USB flash-drive, and memory cards.

Preferably, the integrated fabricator 450 packs each individual wound dressing into a sterile package before discharging the wound dressing at the wound dressing outbox 410. The packages may also be printed with, among others, identification of the wounds, wound dressing instructions, and patient information to help patient or medical practitioners apply the specific wound dressings to specific wound locations for each patient. The printing may also include other general or customized information associated with the patient, the wound and/or the wound dressing. The medical practitioner operating the integrated fabricator 450 may be given the option of choosing the information to be printed on the package.

A diagnostic device (e.g., digital camera) may be coupled to the connector 444 as well. The inputs from such diagnostic device may be stored in the integrated fabricator 450. The inputs from such diagnostic device may also be uploaded to the central server 310 of the electronic medical information system 140. The stored inputs may be reviewed by other medical practitioners to approve or authorize the wound dressing specification or to assist generation of the statistical models for wound treatment.

The integrated fabricator 450 may also download digital images of the wound that was previously stored in the integrated fabricator 450 or received from other devices (e.g., the central server 310 or another wound dressing parameter generator 114).

Figure 4C:
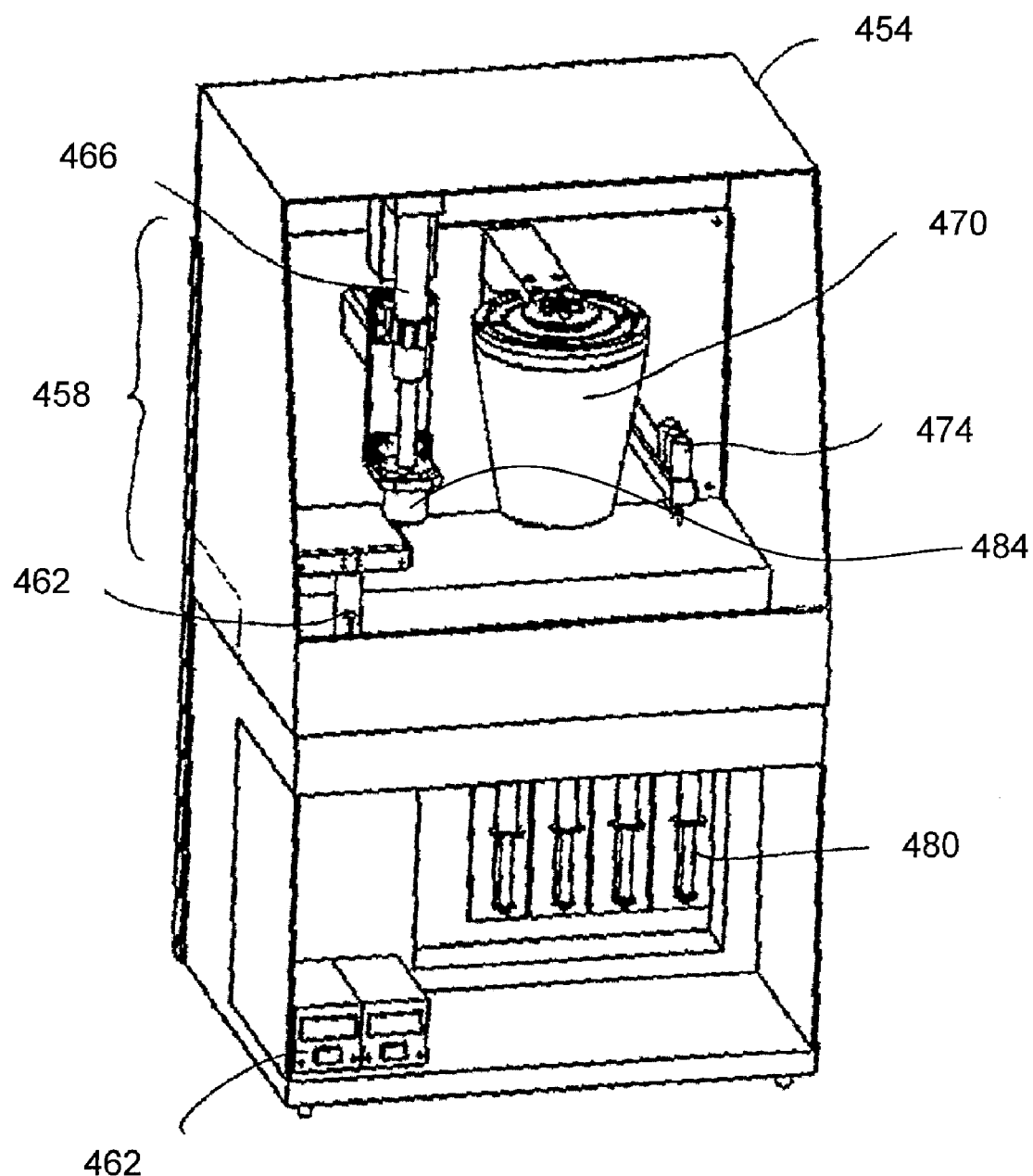
FIG. 4C is a diagram illustrating internal components of the integrated fabricator of FIG. 4B.

FIG. 4C illustrates the integrated fabricator 450 of FIG. 4B where front panels are removed, according to one embodiment. The integrated fabricator 450 includes, among other components, a housing 454, deposition tools 458, and a controller 462. The housing 454 may be a hermetic enclosure that provides a protected environment for the wound dressing fabrication. The ambient pressure inside the enclosure may be kept positive relative to atmospheric pressure to prevent penetration of potentially contaminated air from outside. The enclosure interior may be provided with short wave ultraviolet lamps (not shown) for in-situ sterilization of the internal volume and dressing components.

The deposition tools 458 are installed inside the housing 454 and includes, among other components, a melt film extruder 466, a microfiber electro-spinner 470, and an applicator 474. The melt film extruder 466 and the electro-spinner 470 are used to fabricate the main dressing components. For example, they can be used to fabricate a backing film and a hydrophilic micro-fiber layer of the wound dressings. Cartridges 480 may hold the polymers and/or therapeutic adjuvants (e.g., ointment or cream) that are necessary for the wound dressing fabrication. The cartridges 480 include displacement pumps for controlled delivery of the materials to the deposition tools 458. The controller 462 controls these deposition tools 458.

The melt film extruder 466 is used for fabrication of the backing film of the wound dressing. The melt film extruder 470 includes, among other components, a barrel 484 filled with the polymer and heated to the temperature recommended for extrusion of that polymer. The barrel 484 has an outlet slot or orifice at its bottom for the polymer extrusion under pressure created by an actuator.

The electro-spinner 470 is used for fabrication of the dressing microfiber layer using a fiber electro-spinning technique, for example, as described in U.S. Pat. No. 7,105,058 entitled "Apparatus for Forming a Microfiber Coating," which is incorporated by reference herein in its entirety.

The applicator 474 may be used for application of hydrogel or therapeutic adjuvants (e.g., ointment or cream) or medical adhesive according to the dressing design requirements by dispensing the substances through capillaries. The substance flow rate is provided by corresponding displacement pumps.

Example Wound Dressing Specification

A wound dressing specification includes information for fabricating a wound dressings customized for a specific wound. Referring to FIGS. 1A and 1B, the wound dressing specifications 180 are transferred between the wound dressing parameter generator 114 and the automatic wound dressing fabricator 126A, 126B using mutually agreed upon protocols.

Figure 5:
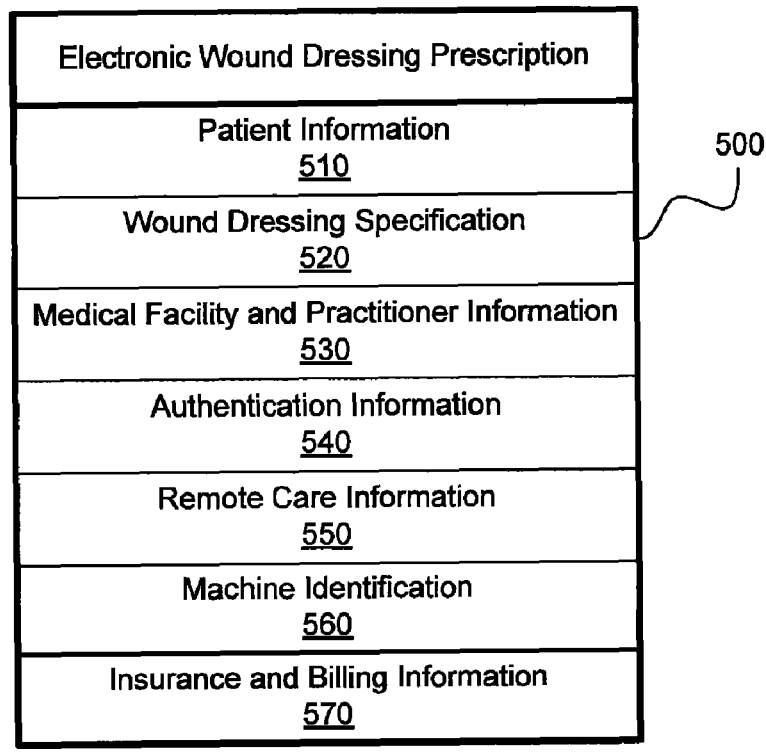
FIG. 5 is a diagram illustrating data fields in an electronic wound dressing prescription according to one embodiment.

Referring to FIG. 5, an electronic wound dressing prescription 500 including the wound dressing specification 520 is illustrated. In the example of FIG. 5, the wound dressing specification 520 is transmitted between the wound dressing parameter generator 114 and the automatic wound dressing fabricator 126A, 126B as part of an electronic wound dressing prescription 500. The electronic wound dressing prescription 500 includes, among other information, patient information 510, the wound dressing specification 520, medical facility and practitioner information 530, authentication information 540, remote care information 550, and machine identification 560.

The patient information 510 is received at the wound dressing parameter generator 114 via the input device 210. Alternatively, minimal information (e.g., patient identification number) about the patient is received at the wound dressing parameter generator 114, and additional information about the patient based on the minimal information is collected from the central server 310 and added to the electronic wound dressing prescription 500. Alternatively, additional information about the patient may be received via the terminal 124. The patient information 510 may include, among others, information such as patient's name, gender, address, phone number, date of birth, and age. The patient information 510 may identify the patient by a unique identifier code that can be tracked by the wound dressing dispenser 120 or the central server 310.

The authentication information 540 is used for verifying that the electronic wound dressing prescription 500 is approved or authorized by a medical practitioner. The authentication information 540 may also identify the medical practitioner who created, edited, updated, and accessed the electronic wound dressing prescription 500. The authentication information 540 may be generated when a medical practitioner reviewing the wound dressing specification inputs a code approving the wound dressing specification via the wound dressing parameter generator 114 or the terminal 124 of the electronic medical information system 140. The approval or authorization by the medical practitioner may be carried out at the wound treatment facility 110 by inputting a code uniquely identifying the medical practical to the wound dressing parameter generator 114 or the terminal 124A. Alternatively, the medical practitioner may remotely review and authorize the electronic wound dressing prescription via remote web services.

The remote care information 550 includes information associated with providing of the wound care of patients at a predetermined location other than the place where the wound dressing specification 180 was generated. Referring to FIGS. 1A and 1B, the wound dressings are fabricated and sent to the predetermined location 150 remote from the wound treatment facility 110 where the wound dressing specification 180 is generated. The remote care information 550 includes, for example, the address or contact information for the predetermined location 150 where the wound dressings are delivered, identify the type of facility or entity to which the wound dressings are delivered, the method that should be used for shipping the wound dressings, the expected time of arrival for shipped the wound dressings, the medical practitioner or facility responsible for providing the remote wound treatment, and any information associated with insurance policy covering such remote wound treatment services.

The machine information 560 indicates the machine that generated the wound dressing prescription. Specifically, the machine information 560 may include machine identification number of the wound dressing parameter generator 114, the time and date when the electronic wound dressing prescription was created, and the identification of the terminal 124 via which the wound dressing specification was sent. The machine information 560 may be used to identify any wound dressing parameter generators that may be malfunctioning or outdated. The machine information 560 may also include the medical practitioner who observed the wound and provided inputs to the wound dressing parameter generator 114.

The insurance and billing information 570 includes insurance information associated with the patient such as the details of the insurance company (identification, name, address, contract person, phone number), the insurance policy group number, plan effective date, plan expiration date, plan type (e.g., Medicare, Medicaid, HMO, or PPO), name of the insured, insured's relationship to the patient, policy number and the reimbursement codes. The insurance and billing information 570 may also include information associated with billing such as where the bills associated with the wound should be sent, and any co-payment or fees the patients are responsible for.

Figure 6:
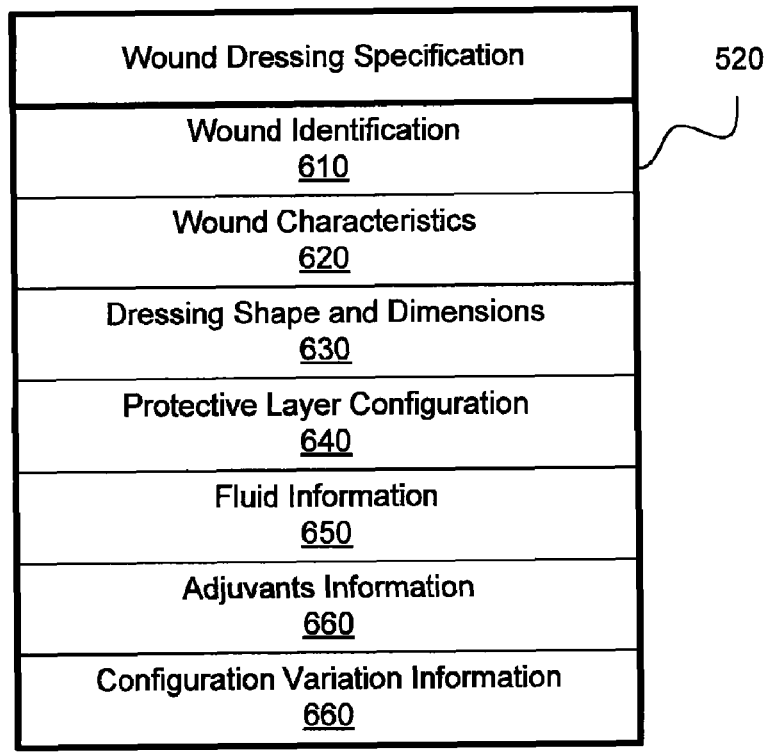
FIG. 6 is a diagram illustrating data fields in a wound dressing specification according to one embodiment.

FIG. 6 is a diagram illustrating data fields in an example wound dressing specification 520, according to one embodiment. The wound dressing specification 520 includes, among others, wound identification 610, wound characteristics 620, dressing shape and dimensions 630, protective layer configuration 640, fluid information 650, adjuvants information 660, and configuration variation information 660. One or more of these data fields in the wound dressing specification 520 may be omitted or substituted with different data fields. Further, additional data fields may also be provided in the wound dressing specification 520.

The wound identification 610 identifies the wound that is being addressed by the wound dressing specification 520. A patient may have two or more wounds, each wound requiring a wound dressing of different configuration. The wound identification 610 indicates which one of the multiple wounds the wound dressing specification 520 pertains to. Various parts of the human body are divided into segments, each segment designated with a different coded number. The coded number may, for example, be CPT (Current Procedural Terminology) codes or ICD-9-CM (International Classification of Diseases, Ninth Revision, Clinical Modification) codes. In such case, the wound identification 610 may indicate a part of the human body where the wound dressing is to be applied. Alternatively, the wound identification 610 may include text information indicating where the wound is located. The wound identification 610 may also indicate how frequently the wound dressing must be replaced (e.g., every two days).

The wound characteristics 620 include, among others, the type of wound, amount of exudates, the type of exudates, the color of exudates, the odor or exudates, dimensions (width, lengths, depth) of the wound, the shape of the wound, tunneling, base color of the wound, the condition of wound edges, amount of necrosis, advancement level, bacteria colonization, epithelialization, sensitivity, severity, health of surrounding skin, periwound properties, pain level, induration, and granulation. The wound characteristics 620 may be received from the medical practitioner observing the wound and/or the digital imaging device of the wound dressing parameter generator 114.

The wound dressing specification 520 may include information 630 on the shape and dimensions of the wound dressings. Note that the shape and dimensions of the wound dressing need not be the same as the shape and dimensions of the wound. The shapes of the wound dressings as indicated by this data field may be oval, circular, rectangular, triangular or other geometric shapes. The shape and dimension information 630 may indicate the shapes and dimensions of the wound dressing in a manner conventionally known The information 630 on the shape and dimensions of the wound dressing also indicate the shapes and dimensions of each layer, if multiple layers are stacked to fabricate the wound dressing.

The protective layer configuration 640 includes information about the protective layer of the wound dressing which forms the outermost layer of the wound dressing. The protective layer configuration 640 includes, among others, the moisture vapor transfer rate (MVTR) of the protective layer.

The fluid information 650 indicates any fluid to be applied to any layers in the wound dressing. The fluid information 650 indicates, among others, the type of fluid (e.g., fluid including growth hormones), the amount of the fluid to be added to the wound dressing, and the layer that should include the fluid.

The adjuvants information 660 indicates the ointment or cream that is to be applied to the wound dressing. The adjuvants information 660 indicates, among others, the type of ointment or cream, and the amount of such ointment or cream to be applied to the wound dressing. The shape/dimension field 630, the protective layer configuration field 640, the fluid information field 650, and the adjuvants information field 660 fields described herein may be stored in various arrangements, for example arranged in the fields as described above, or arranged on a per-layer basis, with the details of each layer specified for each of a plurality of layers.

The configuration variation information 660 describes how the wound dressings should be varied if more than one wound dressings are fabricated for the same wound. For example, different wound dressings may be fabricated for different stages of the wound based on the predicted wound conditions over some period of time. The configuration variation information 660 indicates the variations to be made in the wound dressings for the same wound. Thus, for example, the configuration variation information 660 changes the amount of the fluid in the layer of the wound dressings and reduces the size of the wound dressing as time progresses.

The configuration variation information 660 may be created in various ways. The central server 310 of the electronic medical information system 140 may generate a statistical model of wounds and correlates the progress of the wound conditions with the wound dressings applied thereto. The central server 310 may then generate the configuration variation information 660 based on the statistical model. In other cases, the medical practitioner observing the wound may predict the wound condition and manually indicate the variations to be made in the wound dressings. After the wound dressings are fabricated based on the configuration variation information 660, the packages of the wound dressings may be printed with dates when the wound dressings should be applied to the wound.

The wound dressing specification 520 may omit one or more of the following data fields: the dressing shape and dimensions 630, the protective layer configuration 640, the fluid information 650, the adjuvants information 660, and the configuration variation information 660. In cases where such data fields are omitted, the automatic wound dressing fabricator 126 may generate or reproduce information for data fields based on the wound characteristics 620.

The wound dressing specification 520 may be sent separate from other information in the electronic wound dressing prescription 500. In some embodiments, the wound dressing specification may be sent directly from the wound dressing parameter generator 114 to the automatic wound dressing fabricator 126 while other data of the electronic wound dressing prescription 500 may be processed and sent by the electronic medical information system 140.

The electronic wound dressing prescription 500 or the wound dressing specification 520 may be encrypted to preserve any confidential patient information. In addition, all or parts of the prescription may be digitally signed to ensure that the prescription is not modified from the time the wound dressing prescription 500 is sent to the time that the wound dressing prescription 500 is processed at the fabricator 126.

Method of Providing Wound Treatment Service Using Wound Treatment Facility

Figure 7A:
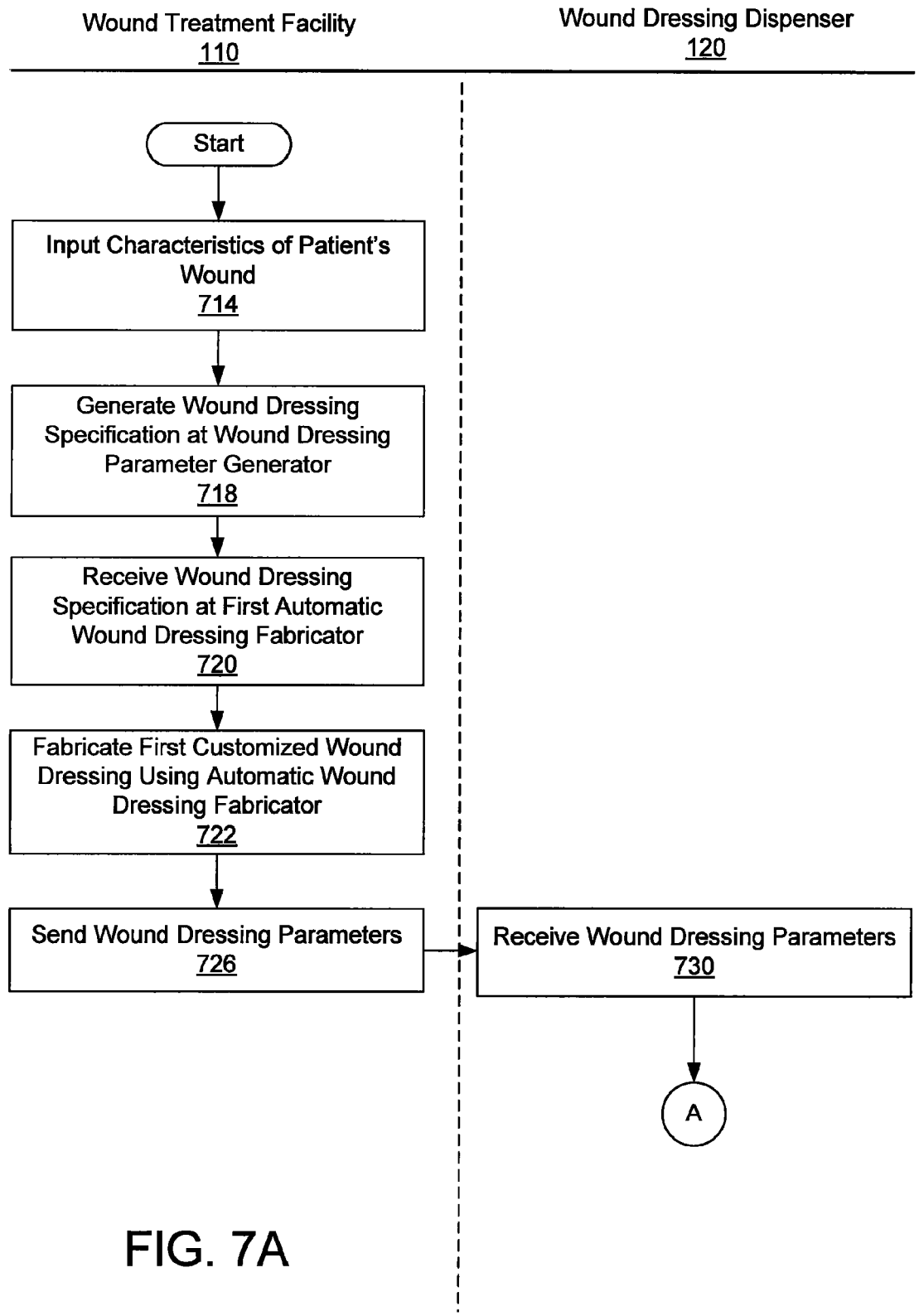
FIGS. 7A and 7B are flow charts illustrating a use case of providing wound treatment services where wounds are diagnosed at a wound treatment facility and wound dressings are delivered from a wound dressing dispenser, according to one embodiment.
Figure 7B:
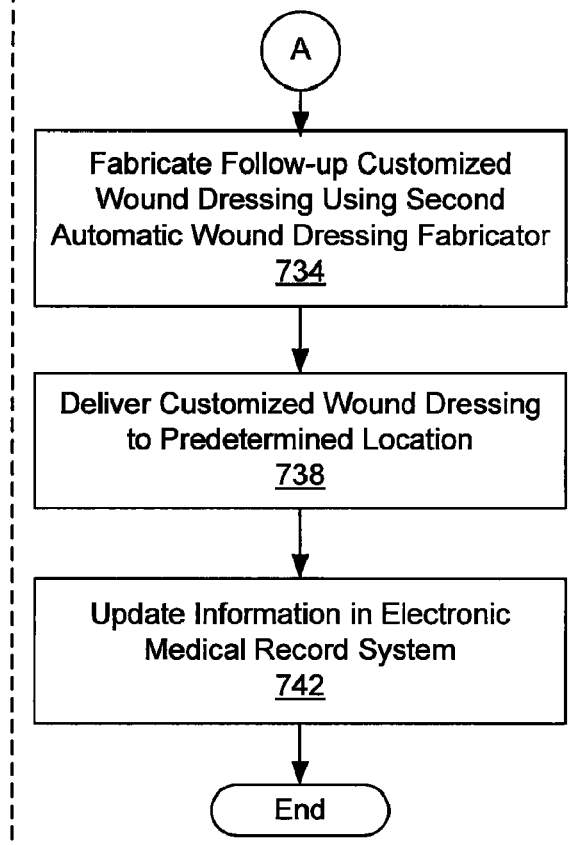
Figure 8A:
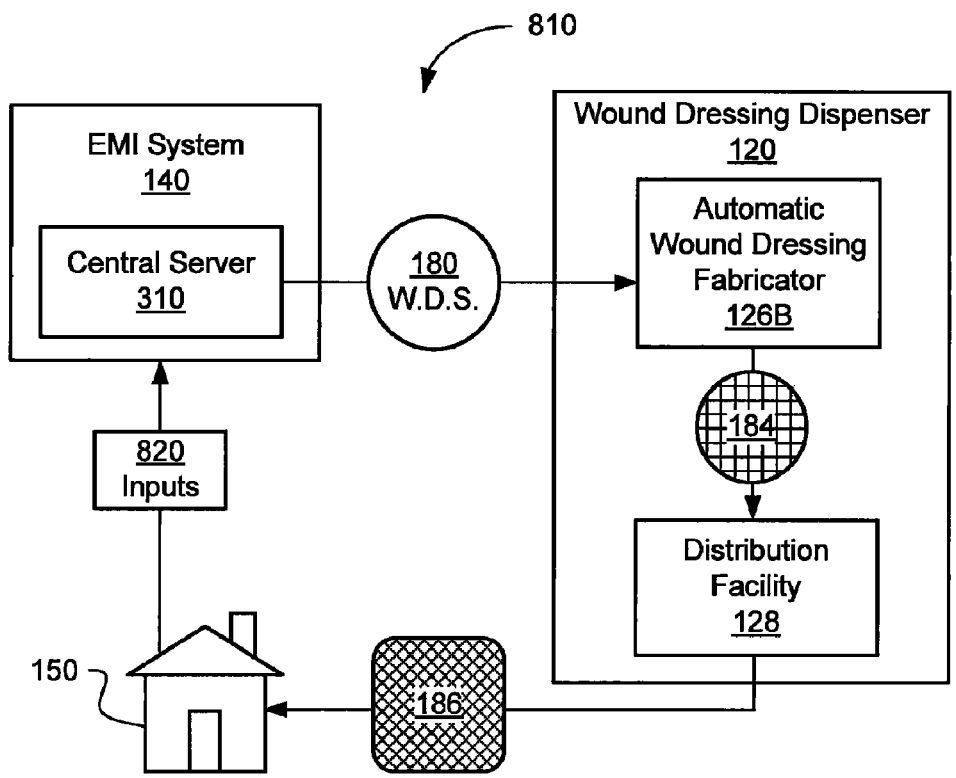
FIG. 8A is a functional block diagram illustrating a wound treatment system where wounds are diagnosed at a predetermined location other than a medical facility and wound dressings are ordered via an electronic medical information system, according to one embodiment.
Figure 8B:
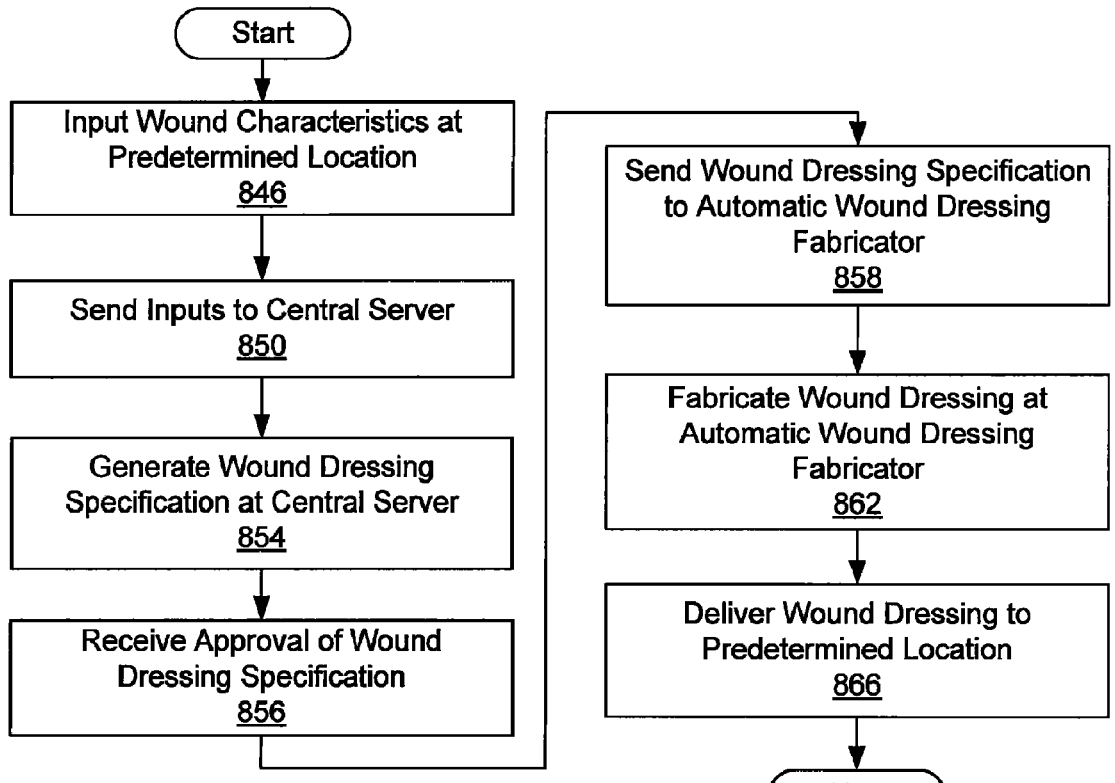
FIG. 8B is a flow chart illustrating a use case for providing wound treatment using the wound treatment system of FIG. 8A, according to one embodiment.

FIGS. 7A and 8B are flow charts illustrating a method of providing wound treatment services according to one embodiment. As a preliminary matter, a patient will be at the wound treatment facility 110, and under the care of a practitioner. The characteristics of the wounds are then diagnosed by observing the wound and/or analyzing the wound using other diagnostic devices. Specifically, the wound dressing parameter generator 114 receives inputs 714 from the medical practitioner and/or other diagnostic devices. Based on such inputs, the wound dressing parameter generator 114 generates 718 the wound dressing specification.

The wound dressing specification is sent to the first automatic wound dressing fabricator 126A installed within the wound treatment facility 110. The first automatic wound dressing fabricator 126A receives 720 the wound dressing specification from the wound dressing parameter generator 114. The first automatic wound dressing fabricator 126A then fabricates 722 a first customized wound dressing based on the received wound dressing specification. The first customized wound dressing may then be applied to the patient's wound by a medical practitioner who may be the same person who input the wound characteristics or a different person.

The wound dressing specification is sent 728 to the remotely located wound dressing dispenser 120 via a communications network or a computer readable storage medium. Then, the wound dressing dispenser 120 receives 730 the wound dressing specification. Information may be added or processed by the electronic medical information system 140 or the wound dressing specification may be approved by medical practitioners and/or the patient before the wound dressing specification 180 is received 730 at the wound dressing dispenser 120.

The second wound dressing fabricator 126B of the wound dressing dispenser 120 fabricates 734 one or more follow-up wound dressings based on the wound dressing specification. The fabricated follow-up wound dressings are then delivered 738 to the predetermined location 150. The predetermined location may be identified in the remote care information 550 data field of the electronic wound dressing prescription 500. The order status information is then updated 742 in the central server 310 to indicate that the wound dressings were delivered to the predetermined location 150.

The steps described above need not be processed in the order described above. Various variations may be made to the illustrative steps. Further, one or more steps may be performed in parallel (e.g., the step 722 and the step 726).

Home Wound Care Embodiments

Wounds need not be diagnosed at the wound treatment facility 110. The wounds may be inspected by medical practitioners visiting the patients at a predetermined location (e.g., patients residence or nearby medical facility). The medical practitioners may access the automatic wound dressing fabricators from a remote location via the Internet or other communication channels to order the wound dressings. The wound dressing may be fabricated by the automatic wound dressing fabricators and then be sent to the predetermined location where the wound dressings may be applied. Embodiments of FIGS. 8A through 10B are related to diagnosing the wounds at a predetermined location other than the wound treatment facility 110, and having the wound dressings delivered to the predetermined location.

FIG. 8A is a functional block diagram illustrating a wound treatment system 810 where wounds are diagnosed at a predetermined location 150 other than a medical facility and wound dressings are ordered via an electronic medical information system 140, according to one embodiment. The medical practitioner visiting the patients may access the electronic medical information system 140 from the predetermined location 150 (e.g., patients' residence) via a data entry system to provide inputs 820 associated with the wound. In the wound treatment system 810, the central server 310 functions as the wound dressing parameter generator that generates the wound dressing specification 180.

The wound specification 180 is then sent to the automatic wound dressing fabricator 126B located within the wound dressing dispenser 120. The wound dressings 184 fabricated and packaged by the automatic wound dressing fabricator 126B are then sent to the distribution facility 128 for delivery to the predetermined location 150. The electronic medical information system 140 and the wound dressing dispenser 120 are essentially the same as described above in detail with reference to FIG. 1B except that the electronic medical information system 140 also functions as the wound dressing parameter generator.

Telemedicine may be implemented by doctors or other medical practitioners accessing the central server 310 to verify the diagnosis of the wound by reviewing the inputs 820 and the wound dressing specification generated by the central server 310. The central server 310 may hold the wound dressing specification 180 until the medical practitioners approves the wound dressing specification 180. After the approval is received, the central server 310 sends the wound specification 180 to the automatic wound dressing fabricator 126B after the approval is received from the doctor or other medical practitioners. In this way, fabrication and dispensing of inappropriate wound dressing based on incorrect diagnosis at the predetermined location 150 may be prevented.

FIG. 8B is a flow chart illustrating a use case for providing wound treatment service using the wound treatment system 810 of FIG. 8A, according to one embodiment. The medical practitioners diagnose wounds at the predetermined location 150 and inputs 846 wound characteristics at the predetermined location 150. The inputs 820 about the diagnosed wounds are then sent 850 to the central server 310. The central server 310 then generates 854 the wound dressing specification 180. The generated wound dressing specification 180 may be reviewed and approved 856 by the medical practitioner. The generated wound dressing specification 180 is then sent 858 to the automatic wound dressing fabricator 126B. The wound dressing 184 is fabricated 862 and then sent to the distribution facility 128 where packages 186 of the wound dressings are delivered 866 to the predetermined location 150.

Figure 9A:
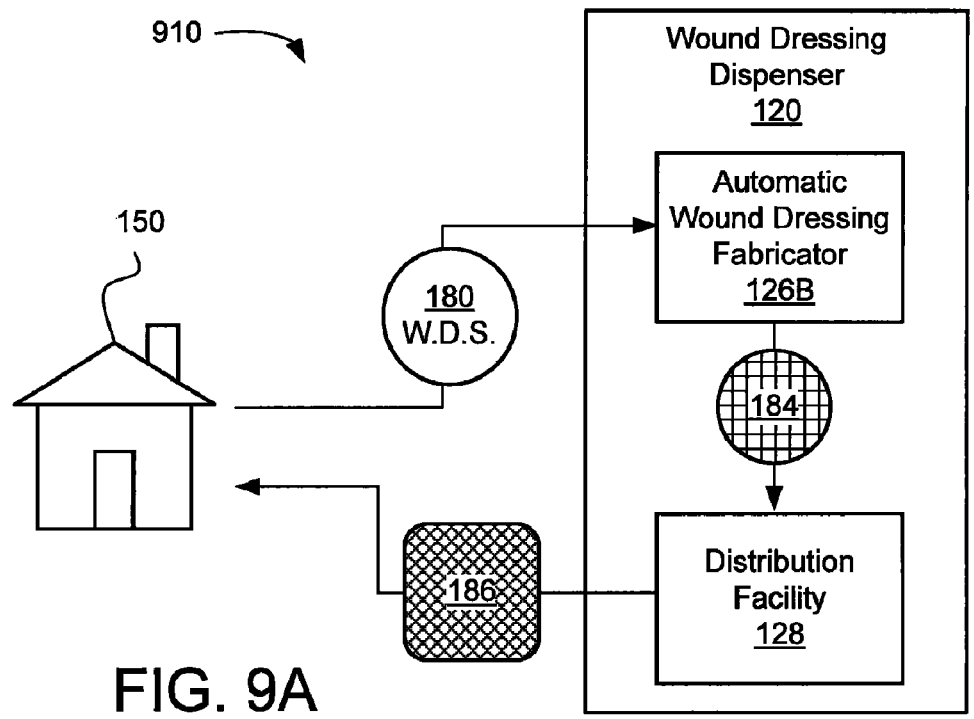
FIG. 9A is a functional block diagram illustrating a wound treatment system where wounds are diagnosed at a predetermined location other than a medical facility and wound dressings are ordered directly from a wound dressing dispenser, according to one embodiment.

FIG. 9A is a functional block diagram illustrating a wound treatment system 910 where wounds are diagnosed at a predetermined location 150 other than a medical facility and wound dressings are ordered directly from a wound dressing dispenser 120, according to one embodiment. The medical practitioners visiting the patients use a computer at the predetermined location 150 to communication with the automatic wound dressing fabricator 126B. The computer stores a software program for generating the wound dressing specification 180 based on the inputs provided by the patients or the visiting medical practitioner. Alternatively, the computer communicates with the automatic wound dressing fabricator 126B to generate the wound dressing specification 180 and send the wound dressing specification 180 to the automatic wound dressing fabricator 126B. That is, the computer in the predetermined location 150 functions as a wound dressing parameter generator. The wound dressing specification 180 is then sent to the automatic wound dressing fabricator 126B for fabricating, packaging and delivering the wound dressing, as described above with reference to FIGS. 1A and 1B.

Figure 9B:
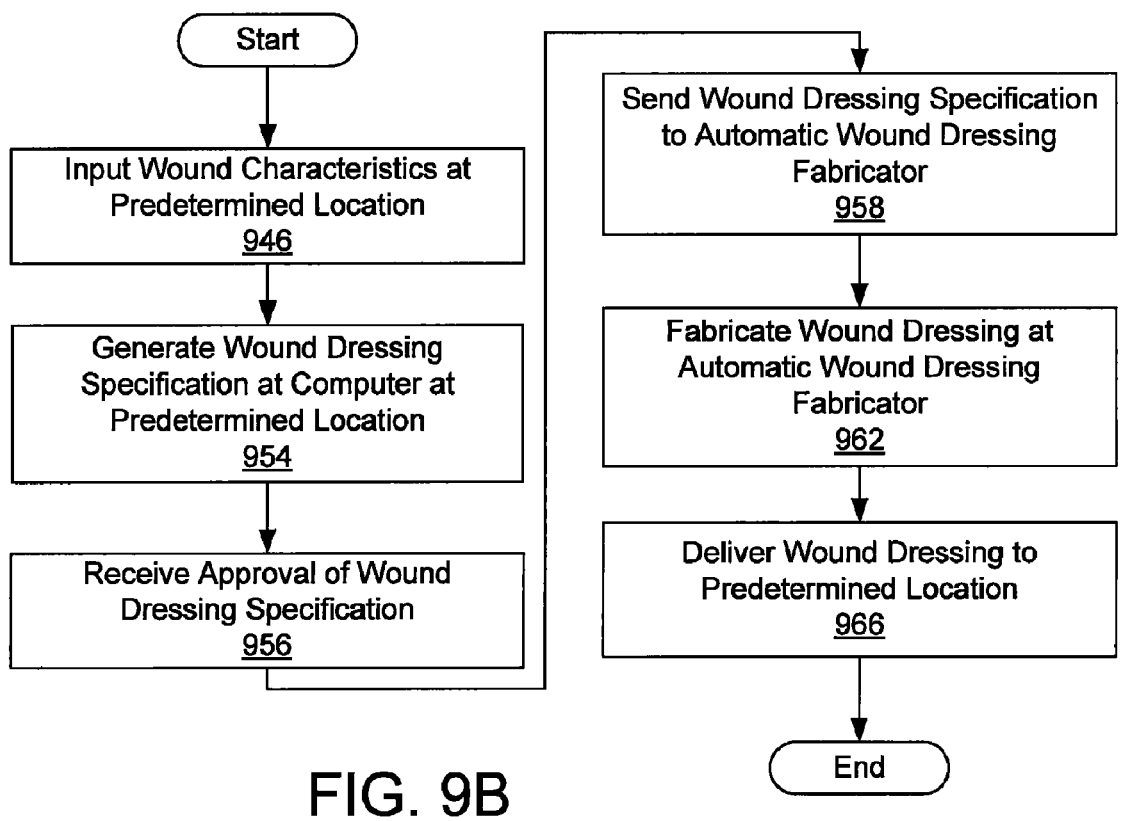
FIG. 9B is a flow chart illustrating a use case providing wound treatment service using the wound treatment system of FIG. 9A, according to one embodiment.

FIG. 9B is a flow chart illustrating a use case providing wound treatment service using the wound treatment system 910 of FIG. 9A, according to one embodiment. The visiting medical practitioners diagnose wounds at the predetermined location 150 and inputs 946 the wound characteristics at the predetermined location. The computer at the predetermined location 150 then generates 954 the wound dressing specification 180. The generated wound dressing specification 180 may be reviewed and approved 956 by the medical practitioner. The generated wound dressing specification 180 is then sent 958 to the automatic wound dressing fabricator 126B via a communications network or a computer readable storage medium. The wound dressing 184 is then fabricated 962 and sent to the distribution facility 128 where packages 186 of the wound dressings are delivered 966 to the predetermined location 150.

Figure 10A:
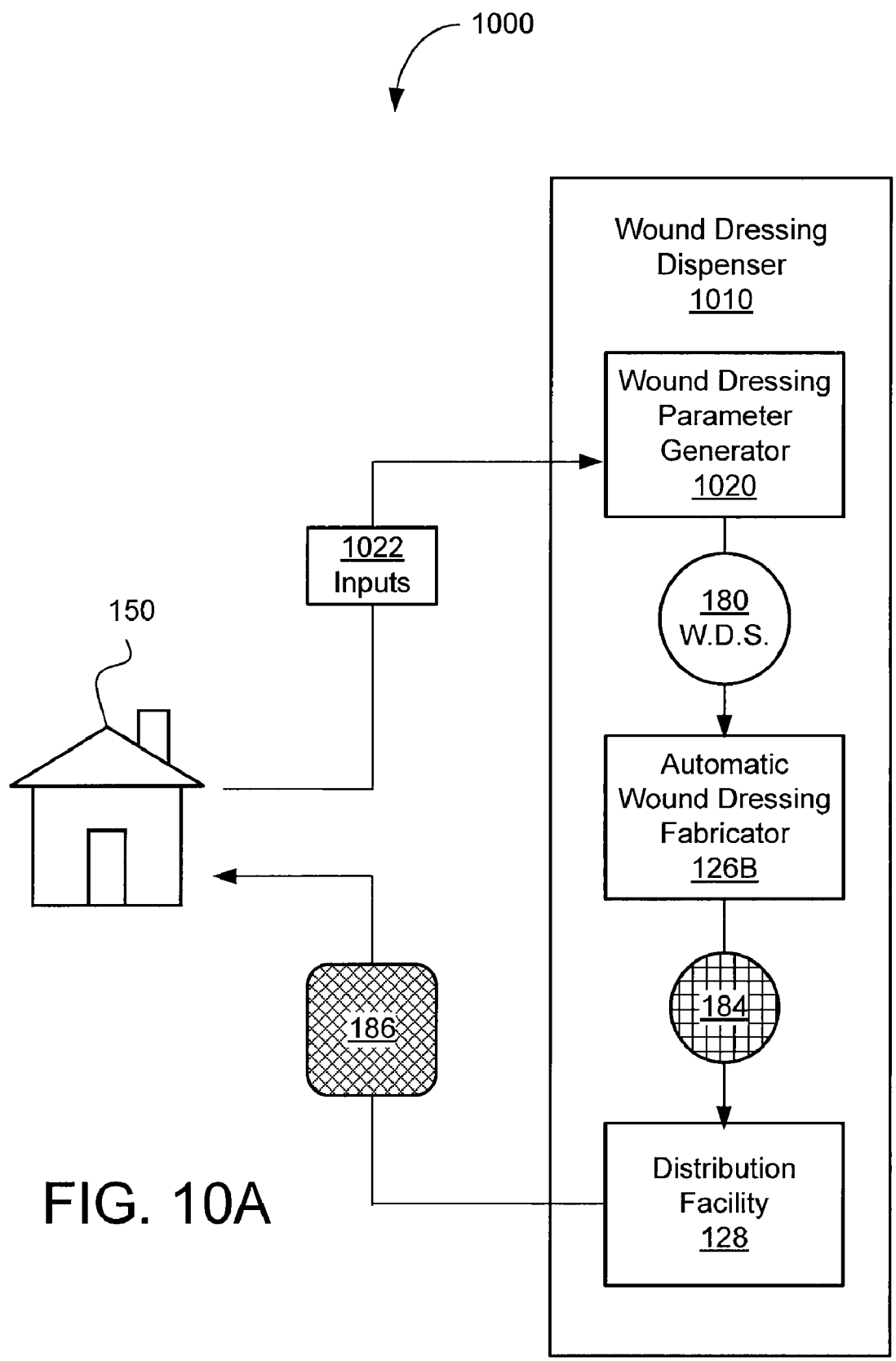
FIG. 10A is a functional block diagram illustrating a wound treatment system where wounds are diagnosed at a predetermined location other than a medical facility and wound dressings are ordered directly from a wound dressing dispenser, according to another embodiment.

FIG. 10A is a functional block diagram illustrating a wound treatment system 1000 where wounds are diagnosed at a predetermined location 150 other than a medical facility and wound dressings are ordered directly from a wound dressing dispenser 1010, according to another embodiment. The embodiment of FIG. 10A is essentially the same as the embodiment of FIG. 9A except that (i) the computer at the predetermined location 150 does not store the software program for generating the wound dressing specification, and (ii)

the wound dressing dispenser 1010 includes a wound dressing parameter generator 1020. Inputs 1022 based on the observation of the wound or the diagnostic devices are sent to the wound dressing parameter generator 1020 via a network (e.g., the Internet) or a computer readable storage medium.

The wound dressing parameter generator 1020 communicates with the computer at the predetermined location 150. The wound dressing parameter generator 1020 may include a gateway server that allows the computer at the predetermined location 150 to communicate with the wound dressing dispenser 1010 via conventional protocols such as TCP/IP (Transmission Control Protocol/Internet Protocol) and HTTP (Hypertext Transfer Protocol).

The wound dressing parameter generator 1020 generates the wound specification 180 and then sends the wound dressing specification 180 to the automatic wound dressing fabricator 126B. The components for the wound dressing parameter generator 1020 and the wound dressing fabricator 126B are essentially the same as described above with reference to FIGS. 2 and 4A.

Figure 10B:
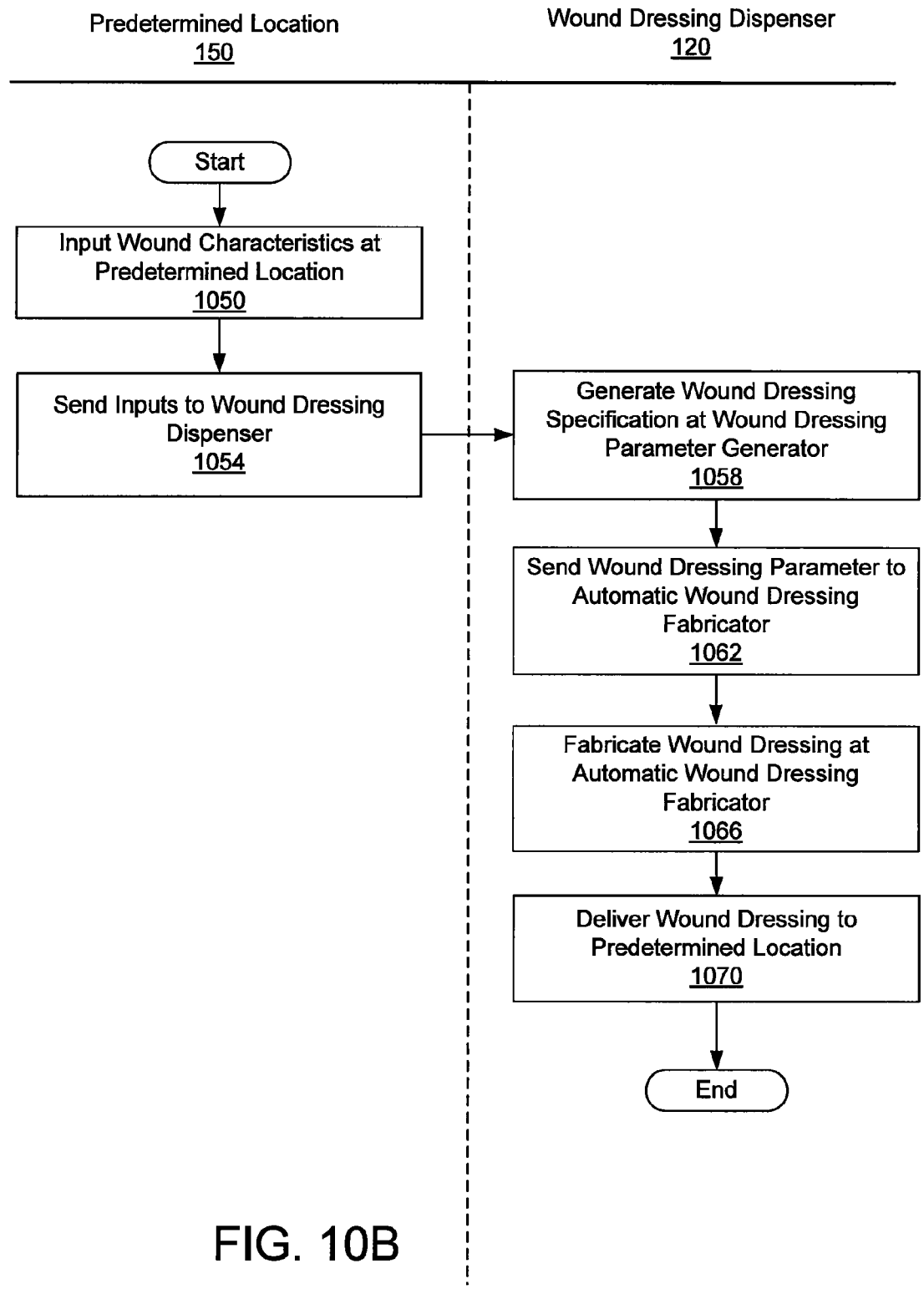
FIG. 10B is a flow chart illustrating a use case providing wound treatment service using the wound treatment system of FIG. 10A, according to one embodiment.

FIG. 10B is a flow chart illustrating a use case of receiving wound treatment service using the wound treatment system 1000 of FIG. 10A, according to one embodiment. The visiting medical practitioners diagnose wounds at the predetermined location 150. The inputs 1022 about the wound characteristics are then provided 1050 to a computer at the predetermined location 150. The computer at the predetermined location 150 then sends 1054 the inputs 1022 to the wound dressing parameter generator 1020 in the wound dressing dispenser 1010 via a communications network or a computer readable storage medium. The wound dressing parameter generator 1020 generates 1058 the wound dressing specification 180. The generated wound dressing specification 180 is then sent 1062 to the automatic wound dressing fabricator 126B. The wound dressing 184 is then fabricated 1066 and then sent to the distribution facility 128 where packages 186 of the wound dressings are delivered 1070 to the predetermined location 150.

In the examples described above with reference to FIGS. 8A through 10C, the configuration algorithm 232 (refer to FIG. 2) may be provided on the central server 310 of the electronic medical information system 140, the computer at the predetermined location 150 or the wound dressing parameter generator 1020 at the wound dressing dispenser 1010. The configuration algorithm is important in remote wound care system because the visiting medical practitioners may be less experienced and lack knowledge about how to configure the wound dressings. The configuration algorithm 232 may be executed on the central server 810, the computer in the predetermined location 150 or the wound dressing parameter generator 840 to guide and assist the visiting medical practitioners configure the wound dressing appropriate for the patients.

Alternative Embodiments

The wound dressing parameter generator also performs financial transactions associated with designing of the wound dressing and fabrication of the wound dressing. The wound dressing parameter generator may, for example, include a credit card reader to charge any expenses associated with the wound treatment services to a credit card. Alternatively, the electronic medical information system 140 may include components for charging credit cards or withdrawing fees from bank accounts for expenses associated with the wound treatment service. This alternative embodiment may be used in "self-service" environments for example, such as pharmacies and convenience stores.

Components of the wound dressing parameter generator 114, the automatic wound dressing fabricators 126, and the electronic medical information system 140 may be implemented in software, firmware, hardware or combinations thereof. The components implemented as software may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims.

What is claimed is:

1. A method of providing a customized wound dressing, comprising:
receiving from a remote device a wound dressing specification indicating configuration of a wound dressing customized for a specific wound of a specific patient and generated after diagnosing of the specific wound of the specific patient, the wound dressing specification specifying at least (i) wound identification indicating the specific wound and the specific patient, (ii) a shape and dimension of the wound dressing, and (iii) fluid information indicating fluid applied to one or more layers in the wound dressing before applying the wound dressing to the specific wound;
in response to receiving the wound dressing specification for the specific wound of the specific patient, fabricating a first wound dressing by a first automatic wound dressing fabrication device by at least adding the fluid to the first wound dressing according to the fluid information; and
causing the first wound dressing to be delivered to a predetermined location where the first wound dressing is applied to the specific wound of the specific patient.

2. The method of claim 1, wherein the remote device is a second automatic wound dressing fabrication device located remotely from the first wound dressing fabrication device.

3. The method of claim 1, wherein the remote device is a server remotely located from the first wound dressing fabrication device, the server storing medical records of the patient, the medical records including a wound prescription associated with the specific wound.

4. The method of claim 1, further comprising:
fabricating a second wound dressing using the first automatic wound dressing fabrication device based on the wound dressing specification, the second wound dressing having a second configuration different from a first configuration of the first wound dressing.

5. The method of claim 4, wherein the second wound dressing is adapted for application to the wound after condition of the wound is progressed by application of the first wound dressing to the wound.

6. The method of claim 1, wherein the predetermined location is at least one of the patient's residence, and a medical facility.

7. The method of claim 1, wherein the wound dressing specification further comprises information on configuration of a protective layer in the first wound dressing.

8. The method of claim 1, wherein the wound dressing specification further comprises information identifying a location of the specific wound on the specific patient.

9. The method of claim 1, further comprising receiving patient information associated with the wound dressing specification.

10. The method of claim 1, further comprising sending tracking information associated with delivery of the first wound dressing.

11. The method of claim 1, further comprising:
receiving an authorization associated with the wound dressing specification from a medical practitioner; and
authenticating the authorization of the medical practitioner before fabricating the first wound dressing by the automatic wound dressing fabrication device.

12. The method of claim 1, further comprising:
receiving a reimbursement code associated with the first wound dressing from the remote device, the reimbursement code representing information required for requesting reimbursement from a paying entity.

13. A method of providing wound treatment service, comprising:
receiving wound characteristics of a specific wound of a specific patient at a wound treatment premise after diagnosing the specific wound of the specific patient;
generating, at a computing device, a wound dressing specification based on the wound characteristics at the wound treatment premise, the wound dressing specification indicating configuration of a wound dressing customized for the specific wound of the specific patient, the wound dressing specification specifying at least (i) wound identification indicating the wound and the patient, (ii) a shape and dimension of the wound dressing, and (iii) fluid information indicating fluid applied to one or more layers in the wound dressing before applying the wound dressing to the specific wound; and
sending the wound dressing specification for the specific wound of the specific patient to a first automatic wound dressing fabrication device located remotely from the wound treatment premise for fabrication of a first customized wound dressing by at least adding fluid to the first customized wound dressing according to the fluid information.

14. The method of claim 13, further comprising:
fabricating a second customized wound dressing based on the wound dressing specification by a second automatic wound dressing fabrication device remotely located from the wound treatment premise; and
applying the second customized wound dressing to the wound of the patient.

15. The method of claim 14, wherein the second dressing is adapted for application to the wound after condition of the wound is progressed by application of the first wound dressing to the wound.

16. The method of claim 13, further comprising:
receiving patient information associated with the wound dressing specification at the wound treatment premise; and
sending the patient information to the first automatic wound dressing fabrication device.

17. The method of claim 13, generating the wound dressing specification comprises:
receiving inputs associated with the wound characteristics at a wound dressing parameter generating device; and
generating the wound dressing specification by applying a computer-implemented algorithm to the received inputs.

18. The method of claim 17, further comprising receiving update information from a server, the computer-implemented algorithm modified by the update information to implement updated policy for treating the wound.

19. The method of claim 13, further comprising:
determining progress of condition of the wound after applying the first wound dressing; and
sending observation of the progress of the wound condition to a server for accumulating and processing statistic data associated with wound treatment.

20. The method of claim 13, wherein diagnosing of the specific wound comprises visually observing the specific wound and scanning the specific wound using a digital imaging device.

21. The method of claim 13, further comprising:
generating a reimbursement code based on the wound characteristics, the reimbursement code representing information required for requesting reimbursement associated with the first customized wound dressing from a paying entity; and
sending the reimbursement code to the first automatic wound dressing fabrication device to allow an entity operating the first would dressing fabrication device to collect fees associated with the first wound dressing from the paying entity.

22. A wound treatment premise, comprising:
a wound dressing parameter generating device adapted to generate a wound dressing specification indicating configuration of a wound dressing customized for a specific wound of a specific patient responsive to receiving inputs representing wound characteristics of the specific wound of the specific patient after diagnosing of the specific wound of the specific patient, the wound dressing specification specifying at least (i) wound identification indicating the specific wound and the specific patient, (ii) a shape and dimension of the wound dressing and (iii) fluid information indicating fluid applied to one or more layers in the wound dressing before applying the wound dressing to the specific wound, the wound dressing parameter generating device further adapted to send the wound dressing specification to a first automatic wound dressing fabrication device located remotely from the wound treatment premise; and
a second automatic wound dressing fabrication device adapted to receive the wound dressing specification for the specific wound of the specific patient and fabricate the wound dressing according to the wound dressing specification by at least adding fluid to the wound dressing according to the fluid information.

23. The wound treatment premise of claim 22, further comprising an electronic medical information system storing information of the specific patient and the wound dressing specification associated with the specific patient.

24. The wound treatment premise of claim 22, wherein the wound dressing parameter generating device runs a computer-implemented algorithm to generate the wound dressing specification based on the inputs.

25. The wound treatment premise of claim 24, wherein the wound dressing parameter generating device is further adapted to receive update information from a server for updating the algorithm for generating the wound dressing specification.

26. The wound treatment premise of claim 22, wherein the wound dressing parameter generating device is further adapted to:

receive patient information associated with the wound specification; and send the patient information to the first automatic wound dressing fabrication device.

27. The wound treatment premise of claim 22, wherein the wound dressing parameter generating device is adapted to receive authorization of a medical practitioner approving the wound dressing specification, the wound dressing parameter generating device adapted to send the authorization to the first automatic wound dressing fabrication device.

28. The wound treatment premise of claim 22, wherein the wound dressing parameter generating device is further adapted to generate a reimbursement code associated with the wound dressing, the reimbursement code representing information required to request reimbursement from a paying entity.

29. A wound dressing dispenser facility, comprising:
an automatic wound dressing fabrication device adapted to fabricate a wound dressing customized for a specific wound of a specific patient responsive to receiving a wound dressing specification indicating configuration of a wound dressing generated after diagnosing the specific wound of the specific patient from a wound dressing parameter generating device located remotely from the automatic wound dressing fabrication device, the wound dressing specification specifying at least (i) wound identification indicating the specific wound and the specific patient, (ii) a shape and dimension of the wound dressing, and (iii) fluid information indicating fluid applied to one or more layers in the wound dressing before applying the wound dressing to the specific wound; and
a distribution facility adapted to cause deliver of the fabricated wound dressing to a predetermined location where the fabricated wound dressing is applied to the specific wound of the specific patient.

30. The wound dressing dispenser facility of claim 29, wherein the predetermined location is at least one of the patient's residence and a medical facility.

31. The wound dressing dispenser facility of claim 29, further comprising a terminal for sending tracking information for fabrication and delivery status of the fabricated wound dressing to a server located remotely from the wound dressing dispenser.

32. The wound dressing dispenser facility of claim 29, wherein the automatic wound dressing fabrication device is adapted to receive and authenticate authorization from a medical practitioner approving the wound dressing specification before fabricating the wound dressing.

33. The wound dressing dispenser facility of claim 29, wherein the automatic wound dressing fabrication device is further adapted to receive a reimbursement code associated with the wound dressing, the reimbursement code representing information required to request reimbursement from a paying entity.

34. A non-transitory computer readable storage medium storing instructions thereon, the instructions when executed by a processor cause the processor to:
receive inputs associated with characteristics of a specific wound of a specific patient after diagnosing the specific wound of the specific patient;
generate a wound dressing specification indicating configuration of a wound dressing customized for the specific wound of the specific patient by an algorithm analyzing the inputs, the wound dressing specification specifying at least (i) wound identification indicating the patient and the wound, (ii) a shape and dimension of the wound dressing, and (ii) fluid information indicating fluid applied to one or more layers in the wound dressing before applying the wound dressing to the wound; and
send the wound dressing specification for the specific wound of the specific patient to an automatic wound dressing fabrication device remotely located from the processor.

35. The computer readable storage medium of claim 34, further comprising instructions to:
receive update information from a server accumulating and analyzing statistical data related to wound treatment, the update information generated based on analysis of the statistical data; and
updating the algorithm according to the update information.

36. The computer readable storage medium of claim 34, further comprising instructions to:
receive patient information associated with the wound dressing specification; and
send the patient information to the automatic wound dressing fabrication device.

37. The computer readable storage medium of claim 34, further comprising instructions to:
receive an input from a medical practitioner authorizing the wound dressing specification before sending the wound dressing specification to the automatic wound dressing fabrication device.

38. The computer readable storage medium of claim 34, wherein the inputs are generated by a digital imaging device.

39. The computer readable storage medium of claim 34, wherein the inputs includes at least one member of the group consisting of: a wound type, an amount of exudation, depth of the wound, a bacteria colonization of the wound, an epithelialization of the wound, and sensitivity of wound.

40. A system for providing wound treatment service to a patient comprising:
a wound treatment premise including an wound dressing parameter generating device adapted for generating a wound dressing specification indicating configuration of a wound dressing customized for a specific wound of a specific person responsive to receiving inputs representing characteristics of the specific wound of the specific patient after diagnosing the specific wound of the specific patient, the wound dressing specification specifying at least (i) wound identification indicating the specific wound and the specific patient, (ii) a shape and dimension of the wound dressing, and (ii) fluid information indicating fluid applied to one or more layers in the wound dressing before applying the wound dressing to the specific wound; and
a wound dressing dispenser adapted to fabricate the customized wound dressing by an automatic wound dressing fabrication device responsive to receiving the wound dressing specification for the specific wound of the specific patient from the wound treatment premise, the automatic wound dressing fabrication device adapted to fabricate the customized wound dressing by at least adding the fluid to the customized wound dressing according to the fluid information, the wound dressing dispenser further causing delivery of the fabricated wound dressing to a predetermined location.

41. The system of claim 40 further comprising:
an electronic medical information system for receiving and storing the wound dressing specification and wound treatment information representing progress of wound conditions, the electronic medical information system analyzing the wound dressing specification and the wound treatment information to generate an algorithm for generating the wound dressing specification.

42. The system of claim 40, wherein the predetermined location is at least one of the patient's residence and a medical facility.

43. The system of claim 40, further comprising an electronic medical information system adapted to send the wound dressing specification to the wound dressing dispenser responsive to receiving authorization of a medical practitioner approving the wound dressing specification.

44. The system of claim 40, wherein the wound dressing parameter generating device is further adapted to generate and send a reimbursement code associated with the customized wound dressing to the wound dressing dispenser, the reimbursement code representing information required to request reimbursement from a paying entity.

* * * * *